(12) United States Patent
Van Rhijn et al.

(10) Patent No.: US 7,795,242 B2
(45) Date of Patent: Sep. 14, 2010

(54) METHODS AND COMPOSITIONS FOR IMMUNOMODULATION

(75) Inventors: Ildiko Van Rhijn, Amsterdam (NL); David C. Young, Haverhill, MA (US); D. Branch Moody, West Roxbury, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1317 days.

(21) Appl. No.: 10/966,874

(22) Filed: Oct. 15, 2004

(65) Prior Publication Data

US 2005/0154053 A1    Jul. 14, 2005

Related U.S. Application Data

(60) Provisional application No. 60/512,383, filed on Oct. 15, 2003.

(51) Int. Cl.
  *A61K 31/34* (2006.01)
  *C07D 307/87* (2006.01)
(52) U.S. Cl. .................. 514/183; 549/462; 514/469
(58) Field of Classification Search ................ None
  See application file for complete search history.

(56) References Cited

U.S. PATENT DOCUMENTS

| | | | |
|---|---|---|---|
| 4,659,709 A | 4/1987 | Harada et al. | |
| 5,679,347 A | 10/1997 | Porcelli et al. | |
| 5,853,737 A | 12/1998 | Modlin et al. | |
| 6,238,676 B1 | 5/2001 | Porcelli et al. | |

OTHER PUBLICATIONS

Van Rhijn et al.,"CD1d-restricted T cell activation by nonlipidic small molecules," PNAS Sep. 14, 2004 vol. 101 (37): 13578-13583.*
Zhang, et al., "Solid-Phase and Solution-Phase Syntheses of Oligomeric Guanidines Bearing Peptide Side Chains," *J. Org. Chem.* vol. 70 pp. 8801-8810 (2005).
Baron et al., "Activation of a Nonclassical NKT Cell Subset in a Transgenic Mouse Model of Hepatitis B Virus Infection," *Immunity*, vol. 16:583-594 (2002).
Giaccone et al., "A Phase I Study of the Natural Killer T-Cell Ligand α-Galactosylceramide (KRN7000) in Patients with Solid Tumors," *Clinical Cancer Research*, vol. 8:3702-3709 (2002).
Gumperz et al., "Murine CD1d-Restricted T Cell Recognition of Cellular Lipids," *Immunity*, vol. 12:211-221 (2000).
Hong et al., "The natural killer T-cell ligand α-galactosylceramide prevents autoimmune diabetes in non-obese diabetic mice," *Nature Medicine*, vol. 7:1052-1056 (2001).
Im et al., "Direct Measurement of Antigen Binding Properties of CD1 Proteins Using Fluorescent Lipid Probes," *The Journal of Biological Chemistry*, vol. 279:299-310 (2004).
Kawano et al., "CD1d-Restricted and TCR-Mediated Activation of $V_\alpha$ 14 NKT Cells by Glycosylceramides," *Science*, vol. 278:1626-1629 (1997).
Koulova et al., "Identification of the Anti-CD3-Unresponsive Subpopulation of $CD4^+$, $CD45RA^+$ Peripheral T Lymphocytes," *The Journal of Immunology*, vol. 145:2035-2043 (1990).
Nakagawa et al., "Antitumor Activity of α-Galactosylceramide, KRN7000, in Mice With EL-4 Hepatic Metastasis and its Cytokine Production," *Oncology Research*, vol. 10:561-568 (1998).
Nieuwenhuis et al., "CD1d-dependent macrophage-mediated clearance of *Pseudomonas aeruginosa* from lung," *Nature Medicine*, vol. 8:588-593 (2002).
Panchomoorthy et al., "A Predominance of the T Cell Receptor Vγ2/Vδ2 Subset in Human Mycobacteria-Responsive T Cells Suggests Germline Gene Encoded Recognition," *The Journal of Immunology*, vol. 147:3360-3369 (1991).
Rosat et al., "CD1-Restricted Microbial Lipid Antigen-Specific Recognition Found in the $CD8^+$ αβ T Cell Pool," *The Journal of Immunology*, vol. 162:366-371 (1999).
Schofield et al., "CD1d-Restricted Immunoglobulin G Formation to GPI-Anchored Antigens Mediated by NKT Cells," *Science*, vol. 283:225-229 (1999).
Sharif et al., "Activation of natural killer T cells by α-galactosylceramide treatment prevents the onset and recurrence of autoimmunce Type 1 diabetes," *Nature Medicine*, vol. 7:1057-1062 (2001).
Toura et al., "Cutting Edge: Inhibition of Experimental Tumor Metastasis by Dendritic Cells Pulsed with α-Galactosylceramide," *The Journal of Immunology*, vol. 163:2387-2391 (1999).
Wasik et al., "Differential Effects of Cytokines on Proliferative Response of Human Cd4+ T Lymphocyte Subsets Stimulated Via T Cell Receptor-Cd3 Complex," *The Journal of Immunology*, vol. 144:3334-3340 (1990).
Wysocki et al., ""Panning" for lymphocytes: A method for cell selection," *Proc. Natl. Acad. Sci.*, vol. 75:2844-2848 (1978).

* cited by examiner

*Primary Examiner*—Brandon J Fetterolf
*Assistant Examiner*—Craig Ricci
(74) *Attorney, Agent, or Firm*—Fish & Richardson P.C.

(57) ABSTRACT

Novel antigens are provided herein. The antigens are associated with recognition of CD1 molecules by T cells. These antigens can be used as antigens, adjuvants or as immunomodulatory agents in a variety of therapeutic and prophylactic applications.

2 Claims, 11 Drawing Sheets a b

FIG. 10

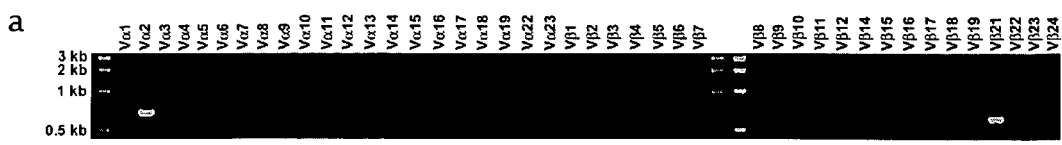

b  α Chain
     1 ATGATGAAAT CCTTGAGAGT TTTACTGGTG ATCCTGTGGC TTCAGTTAAG CTGGGTTTGG
    61 AGCCAACGGA AGGAGGTGGA GCAGGATCCT GGACCCTTCA ATGTTCCAGA GGGAGCCACT
   121 GTCGCTTTCA ACTGTACTTA CAGCAACAGT GCTTCTCAGT CTTTCTTCTG GTACAGACAG
   181 GATTGCAGGA AAGAACCTAA GTTGCTGATG TCCGTATACT CCAGTGGTAA TGAAGATGGA
   241 AGGTTTACAG CACAGCTCAA TAGAGCCAGC CAGTATATTT CCCTGCTCAT CAGAGACTCC
   301 AAGCTCAGTG ATTCAGCCAC CTACCTCTGT GTGGTGAGGT TGGCATCAGG AGGAAGCTAC
   361 ATACCTACAT TTGGAAGAGG AACCAGCCTT ATTGTTCATC CGTATATCCA GAACCCTGAC
   421 CCTGCCGTGT ACCAGCTGAG AGACTCTAAA TCCAGTGACA AGTCTGTCTG CCTATTCACC  (SEQ ID NO: 1)

c  β Chain
     1 ATGGGCACCA GGCTCCTCTG CTGGGTGGCC TTCTGTCTCC TGGTGGAAGA ACTCATAGAA
    61 GCTGGAGTGG TTCAGTCTCC CAGATATAAG ATTATAGAGA AAAAACAGCC TGTGGCTTTT
   121 TGGTGCAATC CTATTTCTGG CCACAATACC CTTTACTGGT ACCTGCAGAA CTTGGGACAG
   181 GGCCCGGAGC TTCTGATTCG ATATGAGAAT GAGGAAGCGG TAGACGATTC ACAGTTGCCT
   241 AAGGATCGAT TTTCTGCAGA GAGGCTCAAA GGAGTAGACT CCACTCTCAA GATCCAGCCT
   301 GCAGAGCTTG GGGACTCGGC CGTGTATCTC TGTGCCAGCA GCCTGACAGG TGGAGAGACC
   361 CAGTACTTCG GGCCAGGCAC GCGGCTCCTG GTGCTCGAGG ACCTGAAAAA CGTGTTCCCA
   421 CCCGAGGTCG CTGTGTTTGA GCCATCAGAA GCAGAGATCT CCCACACCCA AAAGGCCACA  (SEQ ID NO: 2)

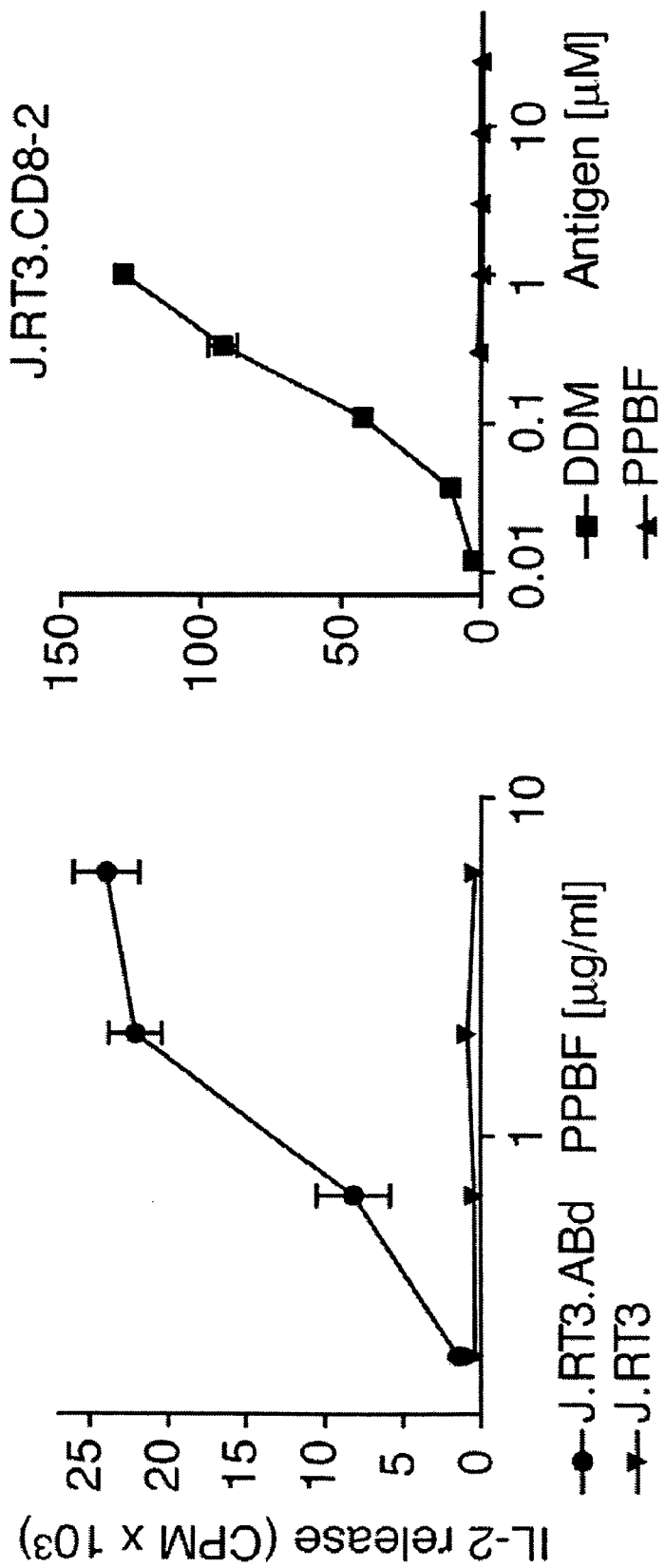

SEQUENCE LISTING

```
<160> NUMBER OF SEQ ID NOS: 3

<210> SEQ ID NO 1
<211> LENGTH: 480
<212> TYPE: DNA
<213> ORGANISM: Homo sapiens

<400> SEQUENCE: 1
atgatgaaat ccttgagagt tttactggtg atcctgtggc ttcagttaag ctgggtttgg      60
agccaacgga aggaggtgga gcaggatcct ggacccttca atgttccaga gggagccact     120
gtcgctttca actgtactta cagcaacagt gcttctcagt ctttcttctg gtacagacag     180
gattgcagga aagaacctaa gttgctgatg tccgtatact ccagtggtaa tgaagatgga     240
aggtttacag cacagctcaa tagagccagc cagtatattt ccctgctcat cagagactcc     300
aagctcagtg attcagccac ctacctctgt gtggtgaggt ggcatcagg aggaagctac     360 atacctacat ttggaagagg aaccagcctt attgttcatc cgtatatcca gaaccctgac     420
cctgccgtgt accagctgag agactctaaa tccagtgaca gtctgtctg cctattcacc      480

<210> SEQ ID NO 2
<211> LENGTH: 480
<212> TYPE: DNA
<213> ORGANISM: Homo sapiens

<400> SEQUENCE: 2
atgggcacca ggctcctctg ctgggtggcc ttctgtctcc tggtggaaga actcatagaa      60
gctggagtgg ttcagtctcc cagatataag attatagaga aaaaacagcc tgtggctttt     120
tggtgcaatc ctatttctgg ccacaatacc ctttactggt acctgcagaa cttgggacag     180
ggcccggagc ttctgattcg atatgagaat gaggaagcgg tagacgattc acagttgcct     240
aaggatcgat tttctgcaga gaggctcaaa ggagtagact ccactctcaa gatccagcct     300
gcagagcttg gggactcggc cgtgtatctc tgtgccagca gcctgacagg tggagagacc     360
cagtacttcg ggccaggcac gcggctcctg gtgctcgagg acctgaaaaa cgtgttccca     420
cccgaggtcg ctgtgtttga gccatcagaa gcagagatct cccacaccca aaaggccaca     480

<210> SEQ ID NO 3
<211> LENGTH: 6
<212> TYPE: PRT
<213> ORGANISM: Artificial Sequence
<220> FEATURE:
<223> OTHER INFORMATION: Syntheticaly generated peptide

<400> SEQUENCE: 3

Leu Lys Lys Arg Arg Leu
 1               5
```

METHODS AND COMPOSITIONS FOR IMMUNOMODULATION

CROSS-REFERENCE TO RELATED APPLICATIONS

This application claims the benefit of priority of U.S. Ser. No. 60/512,383, filed Oct. 15, 2003, the contents of which are hereby incorporated by reference in their entirety.

FEDERALLY SPONSORED RESEARCH OR DEVELOPMENT

The work described herein was funded, in part, through grants from the National Institutes of Health (Grant No. AI50216 and Grant No. AR48632 awarded to D. Branch Moody). The United States government may, therefore, have certain rights in the invention.

TECHNICAL FIELD

This invention relates to CD1 antigens, compositions, cells, and methods relating to the use of hydrophobic antigens for immune modulation.

BACKGROUND

The mammalian immune system is comprised of a complex array of molecular and cellular mediators that recognize and react to microbial antigens. Cell-mediated responses are critical for maintaining immunocompetence. Cell-mediated immune reactions are also thought to be responsible for undesirable responses such as those associated with allergy and certain autoimmune diseases.

T lymphocytes, or T cells, orchestrate cell-mediated immune responses. Antigens derived from polypeptides are presented to T-cells through a group of molecules known as MHC (major histocompatibility complex) molecules. MHC molecules are expressed on the surface of cells in association with small peptide ligands. A receptor on T cells (T cell receptor, or TCR) binds to MHC/peptide complexes on the surface of cells. In general, antigens presented by MHC class I molecules are recognized by $CD8^+$ T-cells, while antigens presented by MHC class II molecules are recognized by $CD4^+$ T-cells.

Antigen presentation to T cells also occurs through a distinct family of antigen presenting molecules, CD1 molecules. These proteins are displayed on antigen-presenting cells which include Langerhans cells, activated B-cells, dendritic cells in lymph nodes, activated blood monocytes, etc. Although there is a structural resemblance to MHC molecules, CD1 molecules differ from MHC molecules in a variety of ways. For instance, CD1 genes are apparently non-polymorphic, while human MHC genes are highly polymorphic, and, unlike MHC molecules, CD1 molecules present non-peptide antigens.

CD1 molecules are a class of antigen presenting molecules that bind lipid antigens, forming CD1-lipid complexes that activate T cells. CD1 proteins are structurally similar to the major histocompatibility complex class (MHC) I molecules, but do not vary substantially in structure within a population, as MHC molecules do. In humans, there are five CD1 proteins, CD1a, CD1b, CD1c, CD1d and CD1e. The CD1d protein has been previously shown to present α-galactosyl ceramide (αGalCer), α-glucosyl ceramide (αGluCer), phosphatidylinositol and glycosylphosphatidylinositol (GPI) to T cells (Kawano, Cui, Koezuka et al. 1997; Schofield, McConville, Hansen et al. 1999; Gumperz, Roy, Makowska et al. 2000). Thus, antigens known to be presented by CD1d are amphipathic glycolipids with two alkyl chains.

CD1-restricted immune responses have been implicated in responses to microbial antigens, and also in the regulation of autoimmune responses. In mice, CD1d-restricted T cells have been shown to mediate tumor rejection (Nakagawa, Motoki, Nakamura et al. 1998; Toura, Kawano, Akutsu, Nakayama, Ochiai, Taniguchi 1999), delay the onset of juvenile diabetes (Sharif, Arreaza, Zucker et al. 2001; Hong, Wilson, Serizawa et al. 2001), and mediate protection from infection by viruses and bacteria (Baron, Gardiner, Nishimura, Shinkai, Locksley, Ganem 2002; Nieuwenhuis, Matsumoto, Exley et al. 2002). αGalCer antigens are in phase I trials of humans with juvenile diabetes and metastatic cancers (Giaccone, Punt, Ando et al. 2002).

SUMMARY

The invention includes novel antigens that modulate the activity of CD1-reactive T cells. One of these antigens is phenyl-2,2,4,6,7-pentamethyldihydrobenzofuran-5-sulfonyl (PPBF). The PPBF molecule is extremely small compared to all other known T cell antigens.

In one aspect, the invention features a composition comprising a compound of formula I

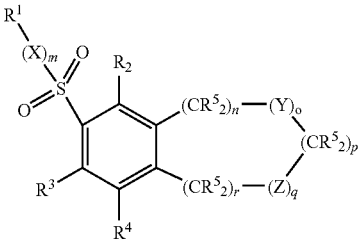

formula I wherein

X is O or $NR^6$;

each of Y and Z independently is O, $NR^6$, or S;

m is 0 or 1;

each of o and q is 0 or 1 and the sum of o and q is 1 or 2;

each of n, p, and r is 0, 1, 2, 3, 4, or 5 and the sum of n, p, and r is 1, 2, 3, 4, or 5;

$R^1$ is hydrogen, alkyl optionally substituted with 1-5 $R^7$, aryl optionally substituted with 1-5 $R^7$, heteroaryl optionally substituted with 1-5 $R^7$;

each of $R^2$, $R^3$, and $R^4$ independently is hydrogen, halogen, nitro, cyano, $OR^6$, $NR^6{}_2$, $CO_2R^6$, $C(O)R^6$, $C(O)NR^6{}_2$, alkyl optionally substituted with 1-5 $R^7$, aryl optionally substituted with 1-5 $R^7$, or heteroaryl optionally substituted with 1-5 $R^7$;

each $R^5$ independently is hydrogen, halogen, nitro, cyano, $OR^6$, $NR^6{}_2$, $CO_2R^6$, $C(O)R^6$, $C(O)NR^6{}_2$, alkyl optionally substituted with 1-5 $R^7$, aryl optionally substituted with 1-5 $R^7$, or heteroaryl optionally substituted with 1-5 $R^7$;

$R^6$ is hydrogen, alkyl optionally substituted with 1-5 $R^7$, aryl optionally substituted with 1-5 $R^6$, heteroaryl optionally substituted with 1-5 $R^7$;

each $R^7$ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl.

In one embodiment, o is 0 and p is 0. In one embodiment, q is 1 and Z is O. In one embodiment, n is 2 and r is 0. In one embodiment, each of $R^2$, $R^3$, and $R^4$ is methyl.

In one embodiment, $R^1$ is

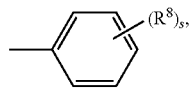

in which s is 0-5 and each $R^8$ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl. In one embodiment, m is 1 and X is O. In one embodiment, $R^8$ is methyl. In one embodiment, m is 0. In one embodiment, $R^8$ is methyl or hydroxyl.

In another embodiment, $R^1$ is

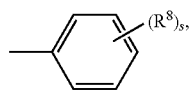

in which s is 0-5 and each $R^8$ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl. In one embodiment, $R^8$ is hydroxyl or alkyl. In one embodiment, each of $R^2$, $R^3$, and $R^4$ is methyl. In one embodiment, X is O. In one embodiment, o is 0 and p is 0. In one embodiment, n is 2 and r is 0.

In one embodiment, the polycyclic compound is one of the following compounds:

Compound 1a (PPBF)

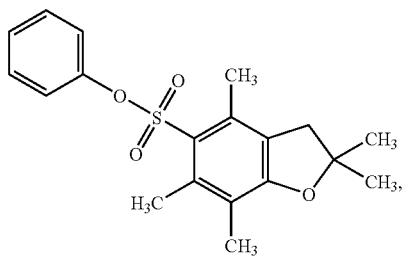

Compound 1b

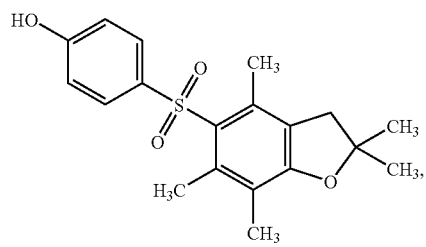

-continued

Compound 1c

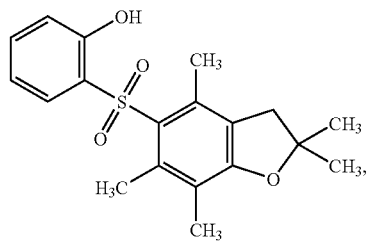

Compound 2

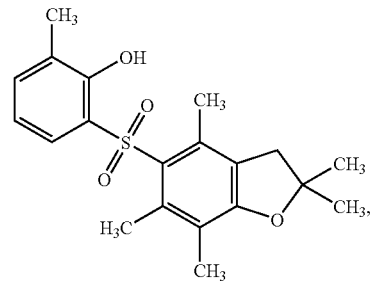

Compound 3

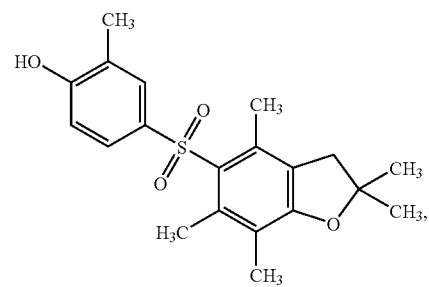

Compound 4

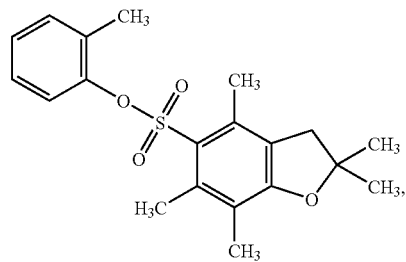

Compound 5

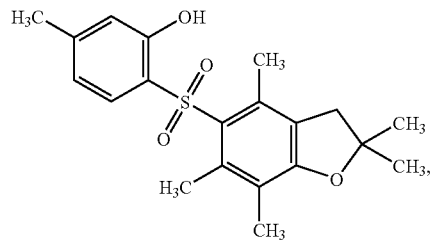

Compound 6

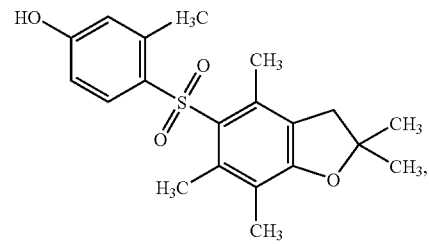

-continued

Compound 7

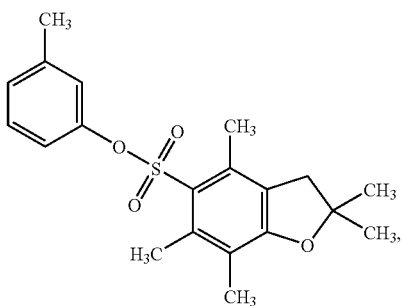

Compound 8

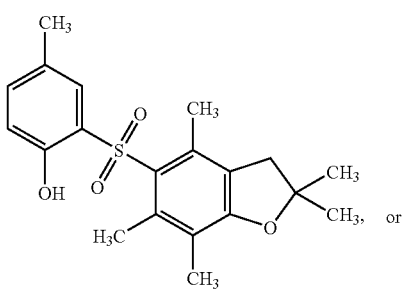
or

Compound 9

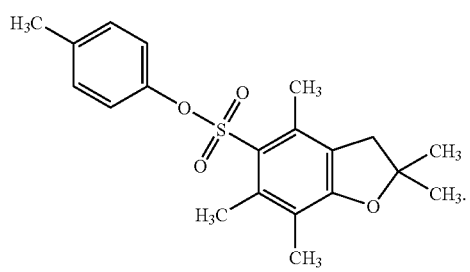

In one embodiment, the compound is compound 1a (PPBF).

In one embodiment, the compound is substantially pure, e.g., the compound is at least 60%, 70%, 75%, 80%, 85%, 90%, 95%, 96%, 97%, 98%, or 99% pure (by dry weight).

The composition can further include a pharmaceutical carrier.

In one embodiment, the compound in present in an amount sufficient to modulate T cell proliferation. In one embodiment, the compound is present in an amount sufficient to modulate an immune response in a subject. In one embodiment, the compound has a biological activity. In one embodiment, the biological activity is modulation of T cell proliferation. In one embodiment, the biological activity is stimulation of T cell proliferation. In one embodiment, the biological activity is inhibition of T cell proliferation. In one embodiment, biological activity is stimulation of T cell proliferation, wherein the compound modulates proliferation of CD1-reactive T cells (e.g., CD1d-reactive T cells).

In one embodiment, the compound is less than 900 MW, less than 800 MW, less than 700 MW, less than 600 MW, less than 500 MW, less than 450 MW, less than 400 MW, less than 375 MW, less than 350 MW, or less than 300 MW.

In one embodiment, the composition further includes an immunomodulatory agent. In one embodiment, the immunomodulatory agent is a cytokine. In one embodiment, the immunomodulatory agent is an adjuvant (e.g., Freund's adjuvant, mycobacterial components, alum). In one embodiment, the immunomodulatory agent is an immunosuppressive drug (e.g., cyclosporine, FK506).

The invention also features pharmaceutical compositions comprising the compounds described herein (e.g., pharmaceutical compositions comprising a compound of formula I, e.g., PPBF or methyl PPBF).

In another aspect, the invention features a method for modulating activity of a T cell, the method including: contacting the T cell with an antigen-presenting cell (APC) and a compound having less than 1000 MW, thereby modulating the activity of the T cell. In one embodiment, the APC comprises CD1 molecules (e.g., CD1d molecules). In one embodiment, the APC is preincubated with the compound prior to contacting the T cell.

In one embodiment, the compound is a polycyclic compound.

In one embodiment, the compound comprises a fused ring structure.

In one embodiment, the compound comprises an aromatic ring structure.

In one embodiment, the compound is a compound of formula I

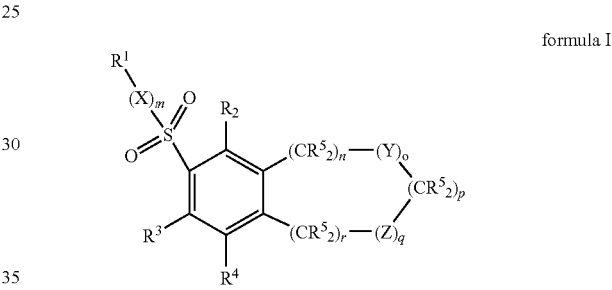

formula I wherein
X is O or $NR^6$;
each of Y and Z independently is O, $NR^6$, or S;
m is 0 or 1;
each of o and q is 0 or 1 and the sum of o and q is 1 or 2;
each of n, p, and r is 0, 1, 2, 3, 4, or 5 and the sum of n, p, and r is 1, 2, 3, 4, or 5;
$R^1$ is hydrogen, alkyl optionally substituted with 1-5 $R^7$, aryl optionally substituted with 1-5 $R^7$, heteroaryl optionally substituted with 1-5 $R^7$;
each of $R^2$, $R^3$, and $R^4$ independently is hydrogen, halogen, nitro, cyano, $OR^6$, $NR^6_2$, $CO_2R^6$, $C(O)R^6$, $C(O)NR^6_2$, alkyl optionally substituted with 1-5 $R^7$, aryl optionally substituted with 1-5 $R^7$, or heteroaryl optionally substituted with 1-5 $R^7$;
each $R^5$ independently is hydrogen, halogen, nitro, cyano, $OR^6$, $NR^6_2$, $CO_2R^6$, $C(O)R^6$, $C(O)NR^6_2$, alkyl optionally substituted with 1-5 $R^7$, aryl optionally substituted with 1-5 $R^7$, or heteroaryl optionally substituted with 1-5 $R^7$;
$R^6$ is hydrogen, alkyl optionally substituted with 1-5 $R^7$, aryl optionally substituted with 1-5 $R^6$, heteroaryl optionally substituted with 1-5 $R^7$;
each $R^7$ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl.

In one embodiment, o is 0 and p is 0. In one embodiment, q is 1 and Z is O. In one embodiment, n is 2 and r is 0. In one embodiment, each of $R^2$, $R^3$, and $R^4$ is methyl.

In one embodiment, $R^1$ is

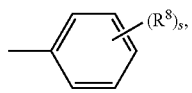

in which s is 0-5 and each $R^8$ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl.

In one embodiment, m is 1 and X is O. In one embodiment, $R^8$ is methyl. In one embodiment, m is 0. In one embodiment, $R^8$ is methyl or hydroxyl.

In one embodiment, $R^1$ is

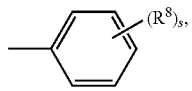

in which s is 0-5 and each $R^8$ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl.

In one embodiment, $R^8$ is hydroxyl or alkyl. In one embodiment, each of $R^2$, $R^3$, and $R^4$ is methyl. In one embodiment, X is O. In one embodiment, o is 0 and p is 0. In one embodiment, n is 2 and r is 0.

In one embodiment, the polycyclic compound is one of the following compounds:

Compound 1a
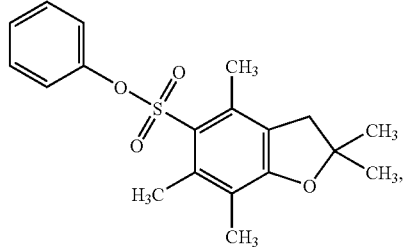

Compound 1b
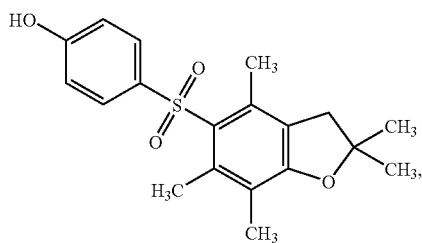

Compound 1c
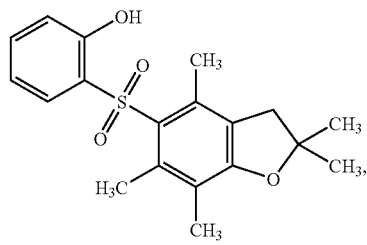

Compound 2
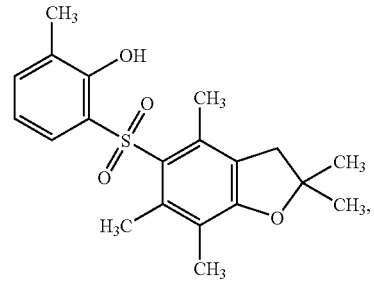

Compound 3
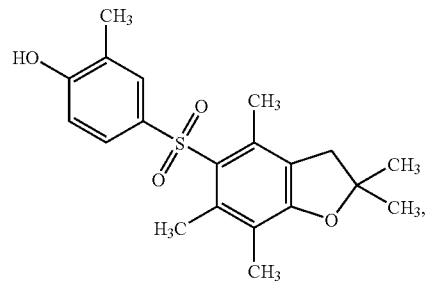

Compound 4
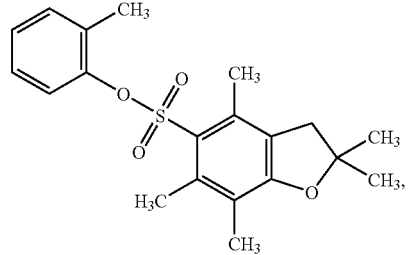

Compound 5
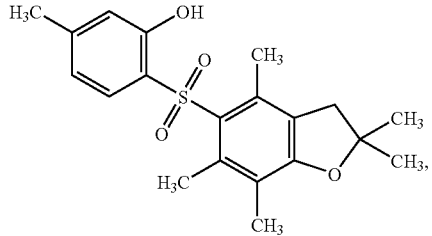

Compound 6
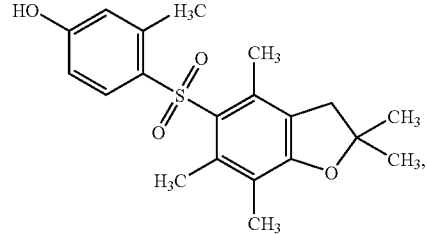

-continued

Compound 7

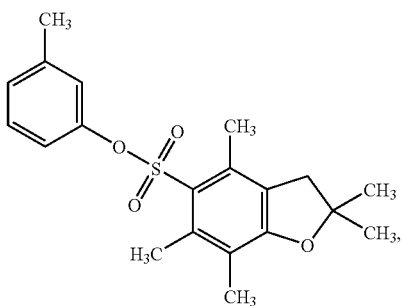

Compound 8

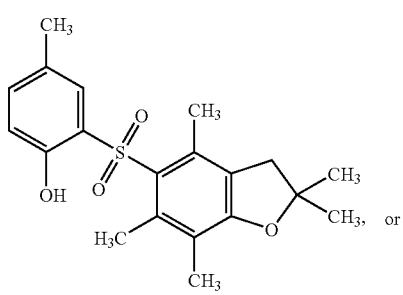

Compound 9

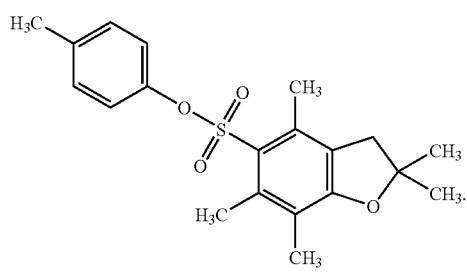

In one embodiment, the compound is a compound of formula II:

formula II

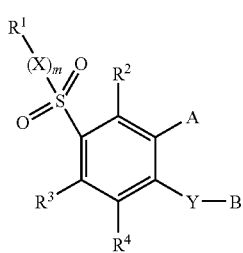

X is O or $NR^6$;

A is hydrogen, alkyl, or aryl; or A and B together represent a $(CR^5_2)_n$ chain;

n is 2, 3, or 4;

Y is O, $NR^6$, N=N, or S; or Y and B together represent heteroaryl optionally substituted with 1-5 $R^7$;

B is hydrogen, alkyl optionally substituted with 1-5 $R^7$, aryl optionally substituted with 1-5 $R^7$, heteroaryl optionally substituted with 1-5 $R^7$, alkylaryl optionally substituted with 1-5 $R^7$, or alkylheteroaryl optionally substituted with 1-5 $R^7$; or B and Y together represent heteroaryl optionally substituted with 1-5 $R^7$; or B and A together represent a $(CR^5_2)_n$ chain;

m is 0 or 1;

$R^1$ is hydrogen, alkyl optionally substituted with 1-5 $R^7$, aryl optionally substituted with 1-5 $R^7$, heteroaryl optionally substituted with 1-5 $R^7$;

each of $R^2$, $R^3$, and $R^4$ independently is hydrogen, halogen, nitro, cyano, $OR^6$, $NR^6_2$, $CO_2R^6$, $C(O)R^6$, $C(O)NR^6_2$, alkyl optionally substituted with 1-5 $R^7$, aryl optionally substituted with 1-5 $R^7$, or heteroaryl optionally substituted with 1-5 $R^7$;

each $R^5$ independently is hydrogen, halogen, nitro, cyano, $OR^6$, $NR^6_2$, $CO_2R^6$, $C(O)R^6$, $C(O)NR^6_2$, alkyl optionally substituted with 1-5 $R^7$, aryl optionally substituted with 1-5 $R^7$, or heteroaryl optionally substituted with 1-5 $R^7$;

$R^6$ is hydrogen, alkyl optionally substituted with 1-5 $R^7$, aryl optionally substituted with 1-5 $R^6$, heteroaryl optionally substituted with 1-5 $R^7$;

each $R^7$ independently is halogen, alkyl, haloalkyl, alkoxy, hydroxy, aryl, heteroaryl, aryloxy, cyano, amino, alkenyl, alkynyl, arylalkyl, or alkoxycarbonyl;

each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl.

In one embodiment, the compound is compound 1a (PPBF).

In one embodiment, the compound is sulfadiazine, celecoxib (Celebrex), sulfisomidine, sulfasalazine, or furosemide.

In one embodiment, T cell activity is modulated in a subject in vivo or ex vivo.

In one embodiment, the subject is at risk for or diagnosed with an infection, an autoimmune disorder, or an allergic disorder.

The invention also features compounds of formula II.

The invention features pharmaceutical compositions comprising compounds of formula II.

In another aspect, the invention features a method for modulating (e.g., inducing, or inhibiting) an immune response in a subject, the method including: identifying a subject in need of modulation of an immune response, and administering to the subject a compound of formula I in an amount effective to modulate an immune response.

In one embodiment, o is 0 and p is 0. In one embodiment, q is 1 and Z is O. In one embodiment, n is 2 and r is 0. In one embodiment, each of $R^2$, $R^3$, and $R^4$ is methyl.

In one embodiment, $R^1$ is

in which s is 0-5 and each $R^8$ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl.

In one embodiment, m is 1 and X is O. In one embodiment, $R^8$ is methyl. In one embodiment, m is 0. In one embodiment, $R^8$ is methyl or hydroxyl.

In one embodiment, $R^1$ is

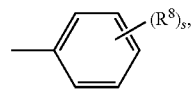

in which s is 0-5 and each $R^8$ independently is halogen, alkyl, haloalkyl, alkoxy, hydroxy, aryl, heteroaryl, aryloxy, cyano, amino, alkenyl, alkyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl.

In one embodiment, $R^8$ is hydroxyl or alkyl. In one embodiment, each of $R^2$, $R^3$, and $R^4$ is methyl. In one embodiment, X is O. In one embodiment, o is 0 and p is 0. In one embodiment, n is 2 and r is 0.

In one embodiment, the polycyclic compound is one of the following compounds:

Compound 1a

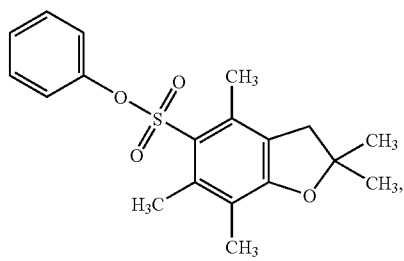

Compound 1b

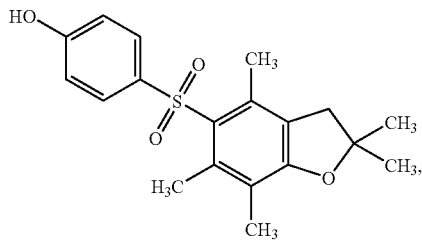

Compound 1c

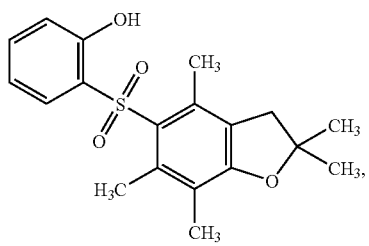

Compound 2

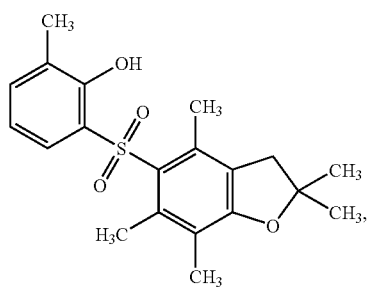

Compound 3

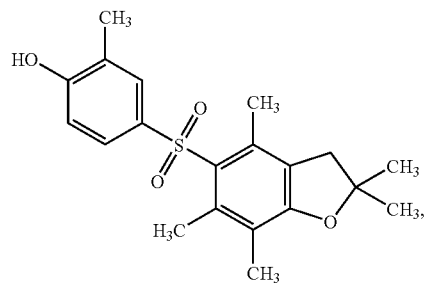

Compound 4

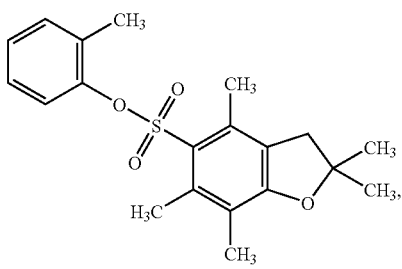

Compound 5

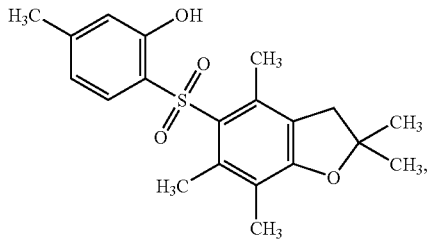

Compound 6

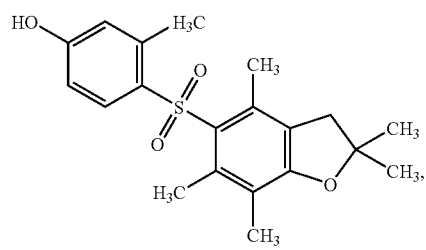

Compound 7

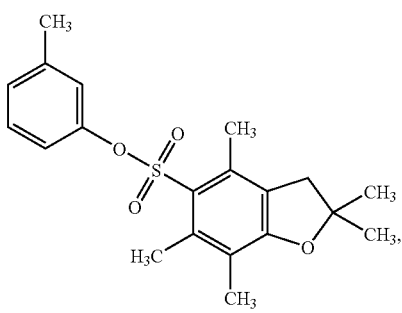

-continued

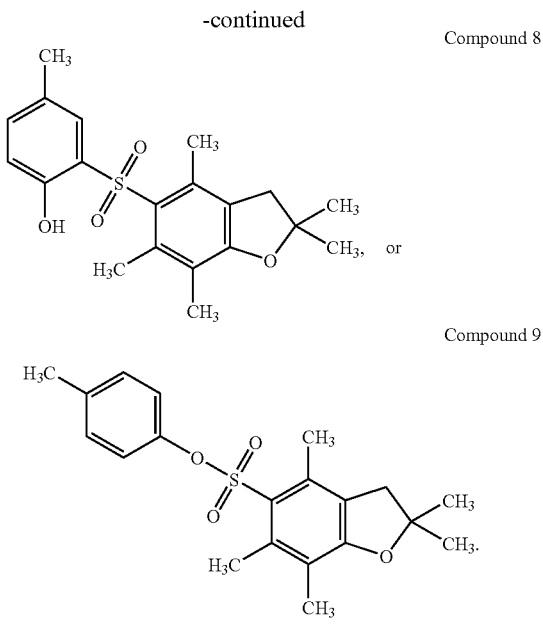

Compound 8

Compound 9

In one embodiment, the compound is a compound of formula II:

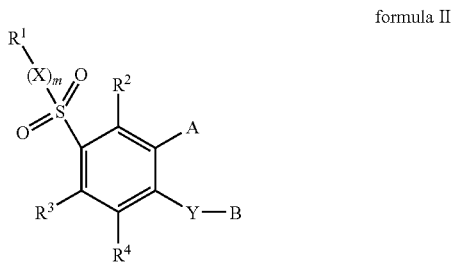

formula II

X is O or $NR^6$;

A is hydrogen, alkyl, or aryl; or A and B together represent a $(CR^5_2)_n$ chain;

n is 2, 3, or 4;

Y is O, $NR^6$, N=N, or S; or Y and B together represent heteroaryl optionally substituted with 1-5 $R^7$;

B is hydrogen, alkyl optionally substituted with 1-5 $R^7$, aryl optionally substituted with 1-5 $R^7$, heteroaryl optionally substituted with 1-5 $R^7$, alkylaryl optionally substituted with 1-5 $R^7$, or alkylheteroaryl optionally substituted with 1-5 $R^7$; or B and Y together represent heteroaryl optionally substituted with 1-5 $R^7$; or B and A together represent a $(CR^5_2)_n$ chain;

m is 0 or 1;

$R^1$ is hydrogen, alkyl optionally substituted with 1-5 $R^7$, aryl optionally substituted with 1-5 $R^7$, heteroaryl optionally substituted with 1-5 $R^7$;

each of $R^2$, $R^3$, and $R^4$ independently is hydrogen, halogen, nitro, cyano, $OR^6$, $NR^6_2$, $CO_2R^6$, $C(O)R^6$, $C(O)NR^6_2$, alkyl optionally substituted with 1-5 $R^7$, aryl optionally substituted with 1-5 $R^7$, or heteroaryl optionally substituted with 1-5 $R^7$;

each $R^5$ independently is hydrogen, halogen, nitro, cyano, $OR^6$, $NR^6_2$, $CO_2R^6$, $C(O)R^6$, $C(O)NR^6_2$, alkyl optionally substituted with 1-5 $R^7$, aryl optionally substituted with 1-5 $R^7$, or heteroaryl optionally substituted with 1-5 $R^7$;

$R^6$ is hydrogen, alkyl optionally substituted with 1-5 $R^7$, aryl optionally substituted with 1-5 $R^6$, heteroaryl optionally substituted with 1-5 $R^7$;

each $R^7$ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl In one embodiment, the compound is compound 1a (PPBF).

In one embodiment, the compound is sulfadiazine, celecoxib (Celebrex), sulfisomidine, sulfasalazine, or furosemide.

In one embodiment, the subject is at risk for or diagnosed with an infection, an autoimmune disorder, or an allergic disorder.

In another aspect, the invention features an isolated CD1-reactive T cell, wherein the CD1-reactive T cell is activated by a polycyclic compound having less than 1000 MW. For example, the T cell is activated by an APC expressing CD1. The CD1 may be present in a complex with the polycyclic compound. The CD1 may not be in a complex with the polycyclic compound, but the presence of both the polycyclic compound and CD1 is required for activation of the T cell.

In one embodiment, the T cell is CD1 d-reactive. In one embodiment, the T cell expresses an αβ T cell receptor. In one embodiment, the T cell is a human T cell.

In one embodiment, the T cell expresses a T cell-receptor comprising amino acid sequences encoded by the nucleic acid sequences of SEQ ID NO: 1 and SEQ ID NO:2.

In one embodiment, the T cell is derived from an IL1AP T cell line. In one embodiment, the T cell is a T cell hybridoma.

In another aspect, the invention features an isolated polypeptide comprising an amino acid sequence at least 80%, 85%, 90%, 95%, 96%, 97%, 98%, 99%, or 100% identical to the amino acid sequence encoded by SEQ ID NO: 1 or SEQ ID NO:2.

In another aspect, the invention features an antigenic composition (e.g., a vaccine) comprising a composition comprising a compound of formula I. In another aspect, the invention features an antigenic composition (e.g., a vaccine) comprising a composition comprising a compound of formula II.

As used herein, the term "alkyl" refers to a straight-chained or branched alkyl group containing 1 to 6 carbon atoms. Examples of alkyl groups include methyl, ethyl, n-propyl, isopropyl, tert-butyl, and n-pentyl.

The term "alkenyl" refers to a straight-chained or branched alkenyl group containing 2 to 6 carbon atoms. Examples of alkenyl groups include vinyl, allyl (2-propenyl), dimethylallyl, and butenyl.

The term "aryl" refers to a hydrocarbon ring system (monocyclic to tricyclic) having at least one aromatic ring. Examples of aryl groups include, but are not limited to, phenyl, naphthyl, and anthracenyl.

The term "heteroaryl" refers to a hydrocarbon ring system (monocyclic to tricyclic) having at least one aromatic ring which contains at least one heteroatom (e.g., O, N, or S) as part of the ring in place of carbon atoms. Examples of heteroaryl groups include, but are not limited to, furyl, pyrrolyl, pyrazolyl, thiophenyl, thiadiazolyl, tetrazolyl, triazolyl, triazinyl, thienyl, oxazolyl, isoxazolyl, imidazolyl, thiazolyl, isothiazolyl, benzimidazolyl, pyridinyl, pyrimidinyl, quinazolinyl, indolyl, indiazolyl, isoindolyl, benzotriazolyl, purinyl, benzothiazolyl, benzoisothiazolyl, and benzothiadiazolyl.

The term "5-membered heteroaryl" refers to a ring system (monocyclic to tricyclic) containing at least one aromatic ring which has 5 ring atoms including one or more heteroatoms (e.g., O, N, or S). Examples of 5-membered heteroaryl include, but are not limited to, furyl, pyrrolyl, pyrazolyl, thiadiazolyl, tetrazolyl, triazolyl, thienyl, oxazolyl, isoxazolyl, imidazolyl, thiazolyl, isothiazolyl, benzimidazolyl, benzotriazolyl, purinyl, benzothiazolyl, benzoisothiazolyl, and benzothiadiazolyl.

The details of one or more embodiments of the invention are set forth in the accompanying drawings and the description below. Other features, objects, and advantages of the invention will be apparent from the description and drawings, and from the claims. All cited patents, patent applications, and references (including references to public sequence database entries) are incorporated by reference in their entireties for all purposes. U.S. Ser. No. 60/512,383 is incorporated by reference in its entirety for all purposes.

DESCRIPTION OF DRAWINGS

FIG. 1A is a graph depicting the proliferative response of polyclonal IL1AP T cells stimulated by dendritic cells (DC) and the LKKRRL mixture, as determined by levels of [$^3$H]-thymidine incorporation (cpm; y-axis). FIG. 1B is a bar graph the proliferative response of IL1AP T cells stimulated in the presence of the LKKRRL mixture and antibodies that block CD1a, CD1b, CD1d, control antibody, and no antibody. FIG. 1C is a bar graph depicting the proliferative response of IL1AP T cells stimulated by the LKKRRL mixture.

FIG. 2A is a plot of absorbance peaks of fractions of the HPLC C18-purified LKKRRL mixture. FIG. 2B is a graph depicting the proliferative response of IL1AP T cells stimulated with fractions of the C18-purified LKKRRL mixture.

FIG. 3A is a graph depicting mass spectral analysis of fraction 9 of the purified LKKRRL mixture. FIG. 3B is a graph depicting tandem mass spectral analysis of fraction 9 of the purified LKKRRL mixture. FIG. 3C depicts the chemical structures of phenyl-2,2,4,6,7-pentamethyldihydrobenzofuran-5-sulfonyl (PPBF) and its collisional daughter ions.

FIG. 5A is a plot of absorbance peaks of fractions of the HPLC-purified synthetic PPBF mixture. Fraction D of the synthetic PPBF mixture co-eluted with fraction 9 of the HPLC-purified LKKRRL mixture. FIG. 5B is a graph depicting the proliferative response of IL1AP T cells stimulated with fractions of the HPLC purified synthetic PPBF mixture. FIG. 5C is a graph depicting tandem mass spectral analysis of the compound present in fraction D of the synthetic PPBF mixture.

FIGS. 6A-6D are graphs depicting tandem mass spectral analysis of PPBF and PPBF analogs synthesized with phenol (FIG. 6A), orthochresol (FIG. 6B), metachresol (FIG. 6C), parachresol (FIG. 6D), and the structures of the compounds. FIG. 6E is a graph depicting the proliferative response of IL1APT cells to the PPBF analogs depicted in FIGS. 6A-D.

FIG. 7A is a graph depicting the proliferative response of IL1AP T cells stimulated by αGalCer, PPBF, or no antigen. Proliferative responses were determined by levels of IL-2 release, measured as a function of proliferation of an IL-2 dependent cell line in the presence of stimulated T cell supernatant (cpm; y-axis). FIG. 7B is a graph depicting the proliferative response of αGalCer, CD1d-reactive T cell clone, J3N.5 stimulated by αGalCer, PPBF, or no antigen.

FIG. 8 contains a graph depicting relative stimulation of NKT cells with PPBF; 3-methyl PPBF, 2,6-anilonapthalene sulfonic acid (ANS); 1,8-ANS; and 2,6-ANS. FIG. 8 also contains a schematic diagram of each of the ANS compounds.

FIG. 9A is a graph depicting flow cytometry analysis of IL1AP T cells stained with either anti-TCRαβ-FITC labeled antibody or a control antibody. FIG. 9B is a graph depicting flow cytometry analysis of IL1AP T cells stained with anti-CD4 or a control antibody.

FIG. 10A-B. T cell receptor usage of IL1AP T cells. FIG. 10A depicts the products of RT-PCR of mRNA from an IL1AP T cell line and T cell clones using primers specific for TCR Vα and Vβ gene families. FIG. 10B contains the nucleotide sequence of a TCR α chain from IL1APT cell lines and clones (SEQ ID NO:1). FIG. 10C contains the nucleotide sequence of a TCR β chain from IL1AP T cell lines and clones (SEQ ID NO:2).

FIG. 11A-B. PPBF recognition is mediated by variable regions of the TCR α and β chains. FIG. 11A is a graph depicting IL-2 release by J.RT3-T3.5 cells transfected with the IL1AP TCR Vα2 and Vβ21 chains (J.RT3.ABD) or with empty vectors (J.RT3.mock) and tested for the ability to release IL-2 upon stimulation with PPBV. FIG. 11B is a graph depicting IL-2 release by J.RT3.T3.5 cells transfected with the TCR α and β chains of the CD8-2 cell line (J.RT3-CD8-2) that recognizes the mycobacterial lipopeptides DDM. J.RT3-CD8-2 cells were tested for IL-2 release in response to stimulation with DDM or PPBF.

Like reference symbols in the various drawings indicate like elements.

DETAILED DESCRIPTION

Figure 1:
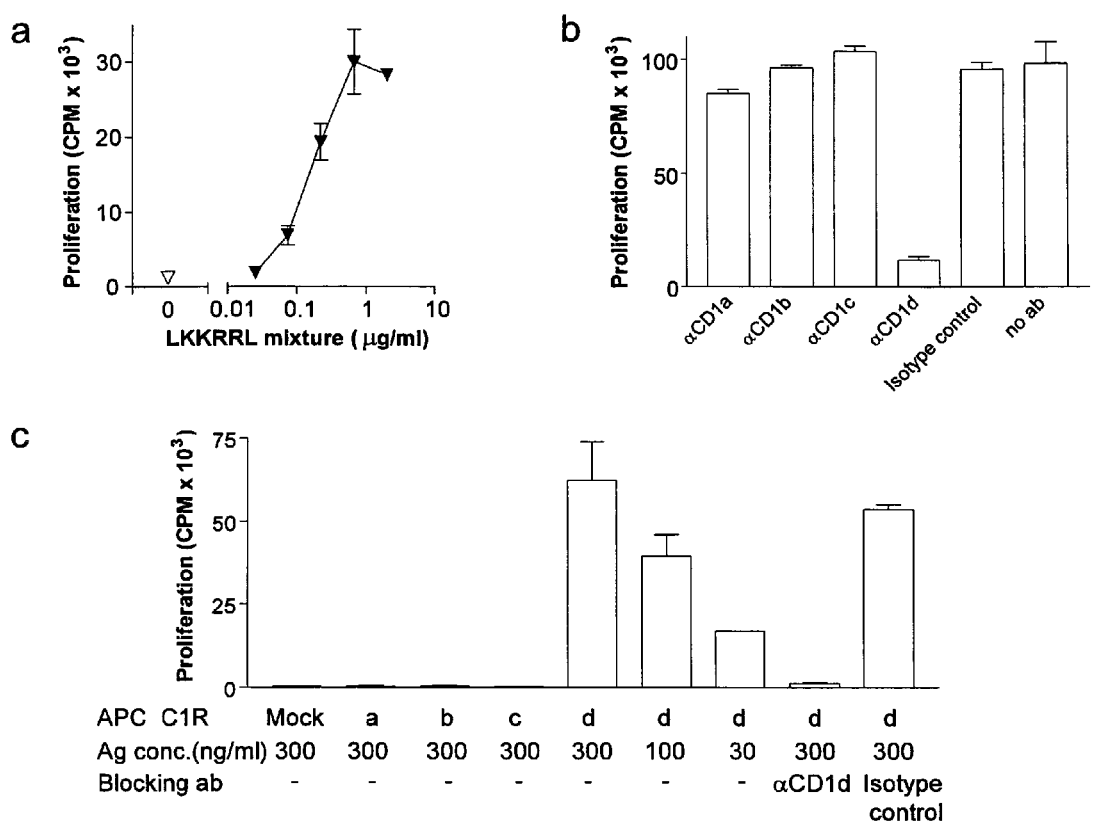
FIG. 1A-C. Activation of T cells by the LKKRRL mixture.

The invention is based, in part, on the discovery of novel antigens recognized by CD1-reactive T cells. One of these antigens is phenyl-2,2,4,6,7-pentamethyldihydrobenzofuran-5-sulfonyl (PPBF). The PPBF molecule is extremely small compared to all other known T cell antigens. Its structure is different from all known CD1-presented antigens, which are lipids with one or two long carbon chains and a hydrophilic head group. The discovery described here expands the known reactivity of CD1 to include molecules composed of polyaromatic hydrocarbons. The antigenic molecules can have less than 1000 MW, 500 MW, 400 MW, or 350 MW. Together this group of structurally related molecules represents a novel class of immunogens for human T cells.

As used herein an "antigen" is a molecule or composition of matter which induces an immune response in an animal. A "foreign antigen" is one that is not endogenously derived in a normal, healthy animal. In an unhealthy animal, however, endogenous molecules or compositions of matter that are expressed as a result of a condition or disease (e.g. cancer, etc.) can be recognized by the immune system as being foreign. Antigens of the invention also include "autoimmune antigens" which are normal, endogenously derived molecules or compositions of matter in an otherwise normal, healthy animal. Autoimmune antigens are also commonly referred to as "self antigens" or "autoantigens".

CD1 Molecules

CD1 molecules are known to present non-peptide antigens such as lipids and glycolipids. These molecules encoded by the genes of the CD1 locus are recognized by selecting CD4⁻ CD8⁻ T-cell clones expressing either α:β or γ:β TCRs (Porcelli, S., et al., *Nature* 341:447-450, 1989; Faure, F., et al., *Eur. J. Immun.* 20:703-706, 1990). Because of the structural resemblance of CD1 molecules, encoded by genes on human chromosome 1, to MHC molecules, encoded by genes on human chromosome 6 (Calabi, F. and Milstein, C., *Nature* 323:540-543, 1986; Balk, S. P., et al., *Proc. Natl. Acad. Sci. USA* 86:252-256, 1989), it has been suggested that CD1 may represent a family of antigen presenting molecules separate from those encoded by the MHC genes (Porcelli, S., et al., *Nature* 341:447-450, 1989; Strominger, J. L., *Cell* 57:895-898, 1989; Porcelli, S., et al., *Immun. Rev.* 120:137-183, 1991).

The five CD1 genes reveal exon and domain structure (α1, α2, α3) that is similar to that of MHC class I genes, yet the proteins are only distantly related in sequence. All CD1 family members share a conserved α3 domain; however, even this domain shows only 32% homology in amino acid sequence with consensus residues of class I MHC α3 domains. A major difference between MHC and CD1 molecules is polymorphism. Human MHC genes are extremely polymorphic: multiple alleles have been described at each known MHC locus. In contrast, CD1 genes are apparently non-polymorphic. Despite these differences, the CD1 molecules, like MHC Class I molecules, are expressed as large subunits (heavy chains) non-covalently associated with β₂-microglobulin (Van Agthoven, A., and Terhorst, C., *J. Immunol.* 128:426-432, 1982; Terhorst, C., et al., *Cell* 23:771-780, 1981).

Four of the five CD1 gene products expressed in humans have been defined serologically, are referred to as CD1a, CD1b, CD1c and CD1d and are distinguished by unique heavy chains with approximate molecular weights of 49 kDa, 45 kDa, 43 kDa and 48 kDa respectively (Amiot, M., et al., *J. Immunol.* 136:1752-1758, 1986; Porcelli, S., et al., *Immunol. Rev.* 120:137-183, 1991; Bleicher, P. A., et al., *Science* 250: 679-682, 1990). CD1 molecules are displayed on a number of APCs including Langerhans cells (which are the major dendritic antigen-presenting cells in the skin), activated B-cells, dendritic cells in lymph nodes, and on activated blood monocytes (Porcelli, S., et al., *Nature* 360:593-597, 1992; Leukocyte Typing IV, Knapp, W., ed., Oxford University Press, Oxford, U.K., pp. 251-269, 1989; Tissue Antigens, Kissmeyer-Nielsen, F., ed., Munksgard, Copenhagen, Denmark, pp. 65-72, 1989).

Presentation of the antigens described herein is associated with a CD1d molecule and, thus, are referred to as being "CD1d-restricted". As used herein, "CD1-restricted antigen" refers to an antigen which is bound by and/or presented with a member of the CD1 family and displayed on the surface of an antigen presenting cell (APC) that expresses the CD1 molecule (also referred to as CD1⁺ cell). The term "CD1-presented antigen" can also be used in place of "CD1-restricted antigen". In addition, when the antigen is bound to a CD1 molecule the antigen can be referred to as "CD1-bound antigen".

As used herein, "displayed" refers to the process of localizing a protein, such as a CD1, or a protein:antigen complex, to the outermost surface of a cell where the protein or protein: antigen complex is accessible to a second cell or to molecules displayed by a second cell. In some instances, antigens are processed with cellular factors in order to be made competent for displaying by an APC. "Antigen presenting cell" is a term well known in the art to include cells which present antigen to T-cells by way of MHC class I molecules and MHC class II molecules, in addition to CD1 molecules. One skilled in the art can use procedures known in the art for determining whether a cell is expressing one or more members of the CD1 family of proteins (see U.S. Pat. Nos. 5,679,347; 5,853,737 and 6,238,676 and Porcelli, S., *Immun. Rev.* 120:137-183, 1991).

The invention, in part, provides several CD1 antigens identified and isolated from synthetic mixtures. The term "isolated" as used herein refers to a molecular species which is substantially free of proteins, lipids, carbohydrates or other materials with which it is normally associated. One skilled in the art can purify lipids, using standard techniques purification such as those described herein.

Novel CD1 Antigens

New antigens have been found to be presented by CD1 molecules, in particular CD1d molecules, and represent another class of CD1 antigens in the form of small polycyclic structures. One category of antigens of the invention have the structure of formula I:

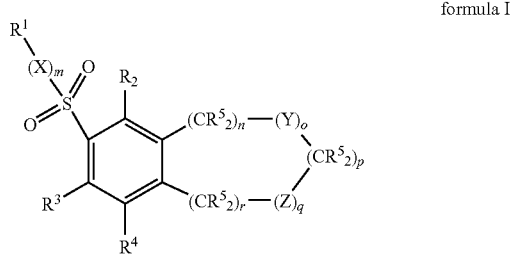

formula I wherein

X is O or NR⁶;

each of Y and Z independently is O, NR⁶, or S;

m is 0 or 1;

each of o and q is 0 or 1 and the sum of o and q is 1 or 2;

each of n, p, and r is 0, 1, 2, 3, 4, or 5 and the sum of n, p, and r is 1, 2, 3, 4, or 5;

R¹ is hydrogen, alkyl optionally substituted with 1-5 R⁷, aryl optionally substituted with 1-5 R⁷, heteroaryl optionally substituted with 1-5 R⁷;

each of R², R³, and R⁴ independently is hydrogen, halogen, nitro, cyano, OR⁶, NR⁶₂, CO₂R⁶, C(O)R⁶, C(O)NR⁶₂, alkyl optionally substituted with 1-5 R⁷, aryl optionally substituted with 1-5 R⁷, or heteroaryl optionally substituted with 1-5 R⁷;

each R⁵ independently is hydrogen, halogen, nitro, cyano, OR⁶, NR⁶₂, CO₂R⁶, C(O)R⁶, C(O)NR⁶₂, alkyl optionally substituted with 1-5 R⁷, aryl optionally substituted with 1-5 R⁷, or heteroaryl optionally substituted with 1-5 R⁷;

R⁶ is hydrogen, alkyl optionally substituted with 1-5 R⁷, aryl optionally substituted with 1-5 R⁶, heteroaryl optionally substituted with 1-5 R⁷;

each R⁷ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl A second category of antigens have the structure of formula II:

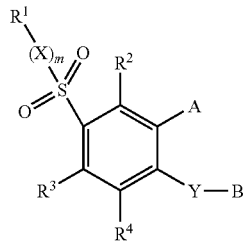

formula II

X is O or NR⁶;

A is hydrogen, alkyl, or aryl; or A and B together represent a $(CR^5_2)_n$ chain;

n is 2, 3, or 4;

Y is O, NR⁶, N=N, or S; or Y and B together represent heteroaryl optionally substituted with 1-5 R⁷;

B is hydrogen, alkyl optionally substituted with 1-5 R⁷, aryl optionally substituted with 1-5 R⁷, heteroaryl optionally substituted with 1-5 R⁷, alkylaryl optionally substituted with 1-5 R⁷, or alkylheteroaryl optionally substituted with 1-5 R⁷; or B and Y together represent heteroaryl optionally substituted with 1-5 R⁷; or B and A together represent a $(CR^5_2)_n$ chain;

m is 0 or 1;

R¹ is hydrogen, alkyl optionally substituted with 1-5 R⁷, aryl optionally substituted with 1-5 R⁷, heteroaryl optionally substituted with 1-5 R⁷;

each of R², R³, and R⁴ independently is hydrogen, halogen, nitro, cyano, OR⁶, NR⁶₂, CO₂R⁶, C(O)R⁶, C(O)NR⁶₂, alkyl optionally substituted with 1-5 R⁷, aryl optionally substituted with 1-5 R⁷, or heteroaryl optionally substituted with 1-5 R⁷;

each R⁵ independently is hydrogen, halogen, nitro, cyano, OR⁶, NR⁶₂, CO₂R⁶, C(O)R⁶, C(O)NR⁶₂, alkyl optionally substituted with 1-5 R⁷, aryl optionally substituted with 1-5 R⁷, or heteroaryl optionally substituted with 1-5 R⁷;

R⁶ is hydrogen, alkyl optionally substituted with 1-5 R⁷, aryl optionally substituted with 1-5 R⁶, heteroaryl optionally substituted with 1-5 R⁷;

each R⁷ independently is halogen, alkyl, haloalkyl, alkoxy, hydroxy, aryl, heteroaryl, aryloxy, cyano, amino, alkenyl, alkynyl, arylalkyl, or alkoxycarbonyl; each of which is optionally substituted with one or more halogen, alkyl, haloalkyl, alkoxy, hydroxy, aryl, heteroaryl, aryloxy, cyano, amino, alkenyl, alkynyl, arylalkyl, or alkoxycarbonyl In some embodiments, these antigens may be synthetic, while in others they may be naturally occurring.

The structure of these antigens is different from known CD1-presented antigens, which are typically lipids with one or two long carbon chains, and a hydrophilic head group.

In one embodiment, the antigen is phenyl-2,2,4,6,7-pentamethyldihydrobenzofuran-5-sulfonyl (PPBF), which has the following structure:

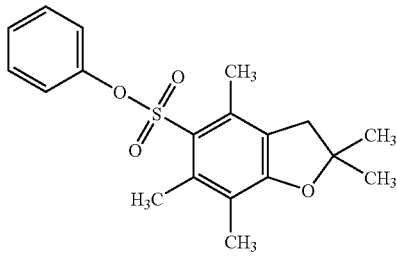

PPBF has certain structural features in common with sulfa drugs, like sulfisomidine, sulfadiazine, sulfasalazine, and celecoxib, which are all known to be strong allergens in humans. In particular, the features that PPBF and sulfa drugs share are the presence of phenyl groups, sulfonyl groups, and a molecular weight under 400 Da. Sulfa drugs and other PPBF-related molecules may also be CD1-presented antigens.

Synthetic antigens may include those derived from nature that have been subsequently manipulated or modified. Alternatively, they include antigens that have no naturally occurring counterparts. For example, the synthetic antigen may contain the heterocyclic scaffold of the Formula I compounds attached (e.g., covalently) to a peptide moiety that may be recognized by a T cell.

The general formula for the antigens is given above as formula I and formula II. It has been shown that the T-cells specifically recognize these antigens.

Methods for isolating the new antigens from a sample are known in the art. As used herein, a "sample" is any solution, emulsion, suspension, or extract which can be tested. Like above, a sample can be first fractionated (subjected to conditions or procedures which separate the components of the sample based on physical or chemical properties such as, but not limited to, size, charge, solubility, or composition) using conventional procedures. Examples of procedures include, but are not limited to, selective precipitation, organic extraction, normal or reverse phase high performance chromatography, and ion exchange chromatography. The fractions of the sample are then tested for the presence of the antigen. The antigens may also be isolated by relying on the binding of CD1d with an antigen of the invention. The CD1d may be purified (and cell free) or it may be cell bound. In one example, a sample containing the antigen is contacted with a purified CD1d. If the CD1d is cell bound, and if the cell is activatable upon binding of CD1d by an antigen, then the antigen can be isolated based on its ability to bind to and activate a CD1d-restricted T cell line (e.g., by exposing a CD1d-expressing antigen presenting cell to an antigen of the invention). As used herein, "contacting" is the process of combining one or more entities. The resulting antigen:CD1d complex or antigen:CD1d⁺ cell complex is then separated and further analyzed (e.g., by dissociating the antigen from the CD1d). Alternatively, the complexes can be further screened for their ability to activate CD1d-restricted T cells. Using such a procedure, a purified CD1d-presented antigen is obtained. To further purify the antigens, either type of complex is treated under appropriate conditions such that the CD1d-bound antigen will be released from the CD1d molecule. The CD1d-presented antigens of the present invention can be purified over a wide range of purities. A skilled artisan will know to employ various purification strategies in order to obtain an antigen which has been purified to the extent required for an intended use.

In addition to the above isolation methods, the antigens provided can be synthesized de novo, as described below in the Examples.

The antigens provided herein were identified with T-cell activation assays performed using purified fractions in order to determine their relative ability to activate T-cells. These assays were carried out essentially as described in U.S. Pat. Nos. 5,679,347; 5,853,737; and 6,238,676, and in Rosat et al. *J. Immunol.* 162:366-371, 1999. Other procedures are well-known in the art.

A "CD1-restricted T-cell" is a mature peripheral blood lymphocyte that expresses T-cell antigen receptors, or is $TCR^+$. CD1-restricted T-cells can recognize a CD1-presented antigen. CD1-restricted T-cells can be $CD4^-$ T-cells which are mature peripheral blood $TCR^+$ lymphocytes which do not express CD4. Techniques for identifying $CD4^-$ T-cells are well known in the art and can readily be employed in the present invention, for example in U.S. Pat. Nos. 5,679,347; 5,853,737 and 6,238,676 and in Panchomoorthy, G., et al., *J. Immuno.* 147:3360-3369, 1991).

Other methods of characterizing classes of T-cells, and of isolating subpopulations of T-cells, have been described. Wysocki, L. J., and Sato, V. L., *Proc Natl Acad Sci. USA* 75:2844-2848, 1978; Wasik, M. A., and Morimoto, C., *J Immunol.* 144:3334-3340, 1990; Harriman, G. R., et al., *J Immunol.* 145:4206-2414, 1990; Koulova, L., et al., *J Immunol.* 145:2035-2043, 1990. Methods of culturing T-cells in vitro, and of immortalizing T-cells via fusion to non-growth restricted cells such as myelomas, have been described. Paul, W. E., et al., *Nature* 294:697-699, 1981; Williams, N., *Nature* 296:605-606, 1982. T-cell populations can be enriched to obtain isolated T-cell clones which are reactive to CD1d-presented antigens. A population of T-cells is allowed to divide and a subpopulation of mixed T-cells is isolated based on proliferation in the presence of $CD1^+$ APCs and CD1-presented antigen, or on cytolytic activity against transfected cells expressing CD1 molecules in the presence of a CD1-presented antigens.

Methods of Use

Formula I and formula II agents can be used in a number of ways including as antigens, adjuvants and immunomodulators. Generally, Formula I and formula II agents act at least in part by modulating (e.g., inducing, or inhibiting) a CD1 immune response, and in particular a CD1d immune response. A "CD1 immune response", as used herein, is an immune response that involves antigen presentation by an antigen presenting cell that expresses a CD1 molecule on its surface to a T-cell that recognizes the presented antigen via its TCR. T-cells that recognize antigen presented in the context of CD1 become activated as a result, and may respond in a number of ways. For example, these T-cells can lyse target cells (e.g., cells infected with bacteria, such as mycobacteria, cells infected with viruses, or cells presenting antigens related to PPBF). T-cells also respond by secreting γ-interferon which in turn can polarize an immune response towards a Th1 response. The antigens therefore are useful in generating effector T-cells.

Previous work has shown also that CD1 molecules are recognized by $CD4^-CD8^-$ T-cell lines derived from patients with SLE (Porcelli, et al., *Nature* 341:447-450, 1989). Leukemia cells expressing CD1 molecules were lysed by the T-cells independent of MHC restriction, even though no foreign (non-self) antigen was present. The T-cells lysed leukemic cells in a CD1-dependent manner in the absence of antigen. Thus, the possibility exists that CD1 molecules play a role in autoimmune diseases.

The CD1 antigens can also be used to modulate an immune response. To "modulate an immune response" as used herein means to enhance or inhibit a pre-existing immune response, to stimulate a non-existent immune response, and/or to alter the characteristics of an immune response. Inhibiting an immune response means that the immune response is lessened from a pre-treatment level, and may include but is not limited to a complete abrogation of an immune response. When the antigens are used to enhance the immunity of a subject, it is intended that the antigens can enhance a pre-existing immune response and/or stimulate a non-existent immune response. If a subject has an infection such as a bacterial infection, then the antigen provided herein may be used to stimulate an immune response and/or enhance a pre-existing immune response. If a subject is undergoing an inappropriate immune response that is associated with the antigen, then administration of the antigen may be used to inhibit or alter the characteristics of the immune response. Altering the characteristics of an immune response can include switching an immune response from a Th2 immune response to a Th1 immune response, or vice versa. As used herein, the term "inhibit" means a reduction in symptoms associated with a condition, or complete elimination of the condition, as determined by a medical practitioner.

Formula I and formula II agents can also be administered together with an adjuvant. In these aspects of the invention, an adjuvant is any molecule or compound which can stimulate the humoral and/or cellular immune response. Adjuvants include, for instance, adjuvants that create a depo effect, immune stimulating adjuvants, adjuvants that create a depo effect and stimulate the immune system, and mucosal adjuvants. In some embodiments, the adjuvants is preferably an immune stimulating adjuvant.

An "adjuvant that creates a depo effect" as used herein is an adjuvant that causes an antigen to be slowly released in the body, thus prolonging the exposure of immune cells to the antigen. Examples include but are not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

An "immune stimulating adjuvant" is an adjuvant that causes activation of a cell of the immune system. It may, for instance, cause an immune cell to produce and secrete cytokines. Examples include but are not limited to saponins purified from the bark of the *Q. saponaria* tree, such as QS21 (a glycolipid that elutes in the $21^{st}$ peak with HPLC fractionation; Antigenics Inc. Woburn, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; O M Pharma S A, Meyrin, Switzerland); and *Leishmania* elongation factor (a purified *Leishmania* protein; Corixa Corporation, Seattle, Wash.).

An "adjuvant that creates a depo effect and stimulates the immune system" is a compound that has both of the above-identified functions. Examples include but are not limited to ISCOMS (immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: Smith-Kline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

A "mucosal adjuvant" as used herein is an adjuvant that is capable of inducing a mucosal immune response in a subject when administered to a mucosal surface in conjunction with an antigen. Examples include but are not limited to bacterial toxins: e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler BD, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of *Borrelia burgdorferi*, outer membrane protine of *Neisseria meningitidis*) (Marinaro et al., 1999, Van de Verg et al., 1996); Oil-in-water emulsions (e.g., MF59) (Barchfield et al., 1999, Verschoor et al., 1999, O'Hagan, 1998); Aluminum salts (Isaka et al., 1998, 1999); and Saponins (e.g., QS21) Aquila Biopharmaceuticals, Inc., Worcester, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micell-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)phosphazene (PCPP polymer; Virus Research Institute, USA) and Leishmania elongation factor (Corixa Corporation, Seattle, Wash.).

Formula I and formula II agents can also be administered to a subject together with a cytokine. Examples of cytokines include, but are not limited to IL-1, IL-2, IL-4, IL-5, IL-6, IL-7, IL-10, IL-12, IL-15, IL-18 granulocyte-macrophage colony stimulating factor (GM-CSF), granulocyte colony stimulating factor (GCSF), interferon-$\gamma$ ($\gamma$-IFN), IFN-$\alpha$, tumor necrosis factor (TNF), TGF-$\beta$, FLT-3 ligand, and CD40 ligand. Cytokines play a role in directing the T-cell response. Helper (CD4$^+$) T-cells orchestrate the immune response of mammals through production of soluble factors that act on other immune system cells, including other T-cells. Most mature CD4$^+$ T helper cells express one of two cytokine profiles: Th1 or Th2. In some embodiments it is preferred that the cytokine be a Th1 cytokine.

The Formula I and formula II agents can also be used as adjuvants given their ability to modulate an immune response. Accordingly, they may be administered together with another antigen (e.g., a CD1 restricted antigen or an MHC restricted antigen) or they may be administered to a subject that is at risk of being exposed to an antigen passively or actively. Subjects that may be passively exposed to an antigen can be one that is in an environment or profession in which exposure to an antigen likely. Examples include being in a country in which particular infectious agents are pandemic, or working in an environment in which infectious agents are common (e.g., a doctor's office or hospital). Active exposure means deliberate exposure to an antigen, such as occurs with a vaccination. Accordingly, the agents of Formula I and formula II may be used in conjunction with vaccine compositions in order to enhance an immune response to the antigen provided in the vaccine. The vaccines as such can be formulated using a purified antigen or can be formulated using a CD1d-bound antigen. Because CD1-restricted antigens are presented to T-cells as a complex of antigen and CD1, the use of an antigen:CD1 complex or an antigen:CD1$^+$ cell complex can, in some cases, provide superior immunization properties. A skilled artisan can employ routine formulation procedures in order to formulate an isolated CD1-presented antigen for use as a vaccine. See Remington's Pharmaceutical Sciences, 18th Ed., Gennaro, A. R., ed., Mack, Easton, (1990); The Pharmacologist Basis of Therapeutics, 7th Ed., Gilman, A. G., et al., eds., MacMillan, N.Y., (1985).

The antigens of the invention can also be used in combination with dendritic cell based vaccines. For example, the antigen can be loaded onto dendritic cells (e.g., autologous dendritic cells), and these cells can then be introduced into a subject. The dendritic cells can also be treated in order to induce CD1d expression.

CD1$^+$ cells (e.g. CD1$^+$ macrophages) used in the various aspects of the invention can naturally express the CD1 molecule or can be manipulated to do so. For instance, cells can be transfected with an expression vector encoding the CD1 molecule of interest. As used herein, "genetically engineered" refers to any human manipulation intended to introduce genetic change. In this instance, cells can be genetically engineered to express a CD1 molecule. In addition, a cell can also be induced to express CD1 by contacting the cell with one or more cytokines. One skilled in the art can readily vary the contacting time, cytokine type and concentration, and contacting conditions to induce CD1, or in particular, CD1d expression. As used herein, "expressing" refers to the process of producing a gene product by transcription of a DNA molecule to generate a corresponding mRNA molecule that is translated into a polypeptide.

The invention provides methods for modulating immune responses in subjects in need thereof. A "subject" shall mean a human or vertebrate animal including but not limited to a dog, cat, horse, cow, pig, sheep, goat, chicken, non-human primate (e.g., monkey), fish (aquaculture species, e.g., salmon), rabbit, rat, and mouse. A subject in need of immunomodulation may be a subject having or at risk of developing a condition that can be therapeutically benefited by an immune response. Examples of conditions include infections such as bacterial, viral, fungal, and parasitic infections, cancers, allergies, asthma, and the like. A subject having one of these conditions can be readily identified by a medical practitioner as these conditions are known and the symptoms associated with each are also known. A subject at risk of developing one of these conditions is similarly readily identified. Examples include subjects that have been exposed or are likely to be exposed to an infectious organism such as a bacterium, virus, fungus, or parasite. Further examples include subjects that have been exposed or are likely to be exposed to a carcinogen, in the case of cancer. Carcinogens are agents with suspected cancer causing activity.

Formula I and formula II agents can therefore be used to treat subjects having or at risk of developing a condition that could benefit from an immune response. As used herein, the term treat includes prevention of a condition by administering the Formula I or formula II agent prophylactically.

Vaccine-induced acquired protective immunity, as used herein, refers to an immunity which occurs as a result of deliberate exposure to an antigen (the compounds of the invention) in a form and dose sufficient to stimulate an immune response to the antigen and, thereby, render the subject immune to subsequent challenge with the antigen. The invention, therefore, provides methods and compositions for enhancing vaccine induced immunity by administering a vaccine comprising an agent of Formula I and/or formula II. Methods for enhancing vaccine-induced protective immunity are useful for the treatment or prevention of a variety of diseases including but not limited to infectious disease (i.e., infections).

As used herein, a "subject in need of treatment" includes a subject having an infection, as well as a subject at risk of developing an infection. Additionally or alternatively, a "subject in need of treatment" embraces a subject having an autoimmune disease, as well as a subject at risk of developing an autoimmune disease.

A subject having an infection or an autoimmune disease is a subject with at least one identifiable sign, symptom, or laboratory finding sufficient to make a diagnosis of an infectious disorder or of an autoimmune disease in accordance with clinical standards known in the art for identifying such disorders. Examples of such clinical standards can be found in *Harrison's Principles of Internal Medicine*, 14th Ed., Fauci A S et al., eds., McGraw-Hill, New York, 1998. In some instances, a diagnosis of an infection will include identification of an infectious organism or agent by culture of the infectious organism or agent from a body fluid or tissue obtained from the subject. Examples of infectious organisms and infectious agents, including but not limited to bacteria, viruses, protozoa, and fungi, are given below.

Examples of infectious bacteria include but are not limited to: *Acinetobacter* spp., *Actinomyces israelli*, *Bacillus anthracis*, *Bacteroides* spp., *Bordetella pertussis*, *Borrelia burgdorferi*, *Brucella melitensis*, pathogenic *Campylobacter* spp., *Clostridium difficile*, *Clostridium perfringens*, *Clostridium tetani*, *Corynebacterium diphtheriae*, other *Corynebacterium* spp., *Enterobacter aerogenes*, *Enterococcus* spp., *Erysipelothrix rhusiopathiae*, *Escherichia coli*, *Francisella tularensis*, *Fusobacterium nucleatum*, *Haemophilus influenzae*, *Helicobacter pylori*, *Klebsiella pneumoniae*, *Legionella pneumophilia*, *Leptospira* spp., *Listeria monocytogenes*, *Mycobacteria* spp. (e.g. *M. tuberculosis*, *M. avium*, *M. gordonae*, *M. intracellulare*, and *M. kansasii*), *Neisseria gonorrhoeae*, *Neisseria meningitidis*, *Nocardia asteroides*, *Nocardia brasiliensis*, *Pasturella multocida*, *Peptostreptococcus* spp., *Proteus* spp., *Pseudomonas aeruginosa*, other *Pseudomonas* spp., *Rickettsia*, *Salmonella* spp., *Serratia* spp., *Shigella* spp., *Staphylococcus aureus*, *Streptobacillus moniliformis*, *Streptococcus* (anaerobic spp.), *Streptococcus* (viridans group), *Streptococcus agalactiae* (Group B *Streptococcu*), *Streptococcus bovis*, *Streptococcus faecalis*, *Streptococcus pneumoniae*, *Streptococcus pyogenes* (Group A *Streptococcus*), *Treponema pallidum*, *Treponema pertenue*, *Vibrio cholerae*, other *Vibrio* spp., and *Yersinia* spp.

Examples of infectious viruses include but are not limited to: Adenoviridae (most adenoviruses); Arena viridae (hemorrhagic fever viruses); Birnaviridae; Hepadnaviridae (Hepatitis B virus); Bungaviridae (e.g., Hantaan viruses, bunga viruses, phleboviruses and Nairo viruses); Calciviridae (e.g., strains that cause gastroenteritis); Coronaviridae (e.g., coronaviruses); Filoviridae (e.g., ebola viruses); Flaviridae (e.g., dengue viruses, encephalitis viruses, yellow fever viruses); Herpesviridae (herpes simplex virus (HSV) 1 and 2, varicella zoster virus, cytomegalovirus (CMV), herpes virus; Iridoviridae (e.g., African swine fever virus); Orthomyxoviridae (e.g., influenza viruses); Paramyxoviridae (e.g., parainfluenza viruses, mumps virus, measles virus, respiratory syncytial virus); Parvovirida (parvoviruses); Papovaviridae (papilloma viruses, polyoma viruses); Picornaviridae (e.g., polio viruses, hepatitis A virus; enteroviruses, human Coxsackie viruses, rhinoviruses, echoviruses); Poxviridae (variola viruses, vaccinia viruses, pox viruses); Reoviridae (e.g., reoviruses, orbiviurses and rotaviruses); Retroviridae (e.g., human immunodeficiency viruses, such as HIV-1 (also referred to as HTLV-III, LAV or HTLV-III/LAV, or HIV-III, and other isolates, such as HIV-LP; Rhabdoviridae (e.g., vesicular stomatitis viruses, rabies viruses); Togaviridae (e.g., equine encephalitis viruses, rubella viruses); and unclassified viruses (e.g., the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Examples of infectious fungi include but are not limited to: *Aspergillus* spp., *Blastomyces dermatitidis*, *Candida albicans*, other *Candida* spp., *Coccidioides immitis*, *Cryptococcus neoformans*, *Histoplasma capsulatum*, and *Rhizopus* spp.

Other infectious organisms include but are not limited to: *Plasmodium* spp. (e.g., *Plasmodium falciparum*, *Plasmodium knowlesi*, *Plasmodium malariae*, *Plasmodium ovale*, and *Plasmodium vivax*), *Babesia divergens*, *Babesia microti*, *Chlamydia trachomatis*, *Giardia* spp., *Leishmania braziliensis*, *Leishmania donovani*, *Leishmania major*, *Leishmania tropica*, *Toxoplasma gondii*, *Trichinella spiralis*, and *Trypanosoma cruzi*.

A subject at risk of developing an infection is a subject with an identifiable risk factor for developing an infection. For example, a subject at risk of developing an infection can include an individual with a known or suspected exposure to another individual with an infection (e.g., medical or military personnel). Alternatively, a subject at risk of developing an infection can include an individual with a known or suspected exposure to an agent or vector associated with an infection. Yet other examples of a subject at risk of developing an infection include a subject that is immunocompromised; a subject about to undergo surgery; and a subject that has recently undergone surgery.

A subject that is immunocompromised is a subject with reduced capacity to mount an effective immune response to an infectious agent. Such subjects may have, for example, an immune system that is immature or that is suppressed in association with exposure to certain pharmacological agents, suppressed in association with exposure to irradiation, suppressed in association with a chromosomal defect, suppressed in association with a hereditary or inborn metabolic defect or enzyme deficiency, suppressed in association with an antibody deficiency, suppressed in association with a defect in the ability of T cells to process and/or present antigen, suppressed in association with a nutritional deficiency, suppressed in association with an infection that directly affects cells of the immune system (e.g., HIV), suppressed in association with a neoplasm. These and other examples of conditions that cause a subject to be immunocompromised can be found in *Harrison's Principles of Internal Medicine*, 14th Ed., Fauci A S et al., eds., McGraw-Hill, New York, 1998.

Thus, in one aspect the invention is useful whenever it is desirable to treat or prevent infection in a subject. This includes prophylactic treatment to prevent such infections in planned surgical procedures, as well as in emergency surgical situations, especially those involving intraabdominal surgeries. Intraabdominal surgeries include, for example: right hemicolectomy; left hemicolectomy; sigmoid colectomy; subtotal colectomy; total colectomy; cholecystectomy; gastrectomy; nephrectomy; vascular repair, including resection of abdominal aortic aneurysm; abscess drainage. Emergency surgeries include, in addition to any of the above, those to correct the following conditions: perforated ulcer (duodenal or gastric); perforated diverticulitis; obstructive diverticulitis; acute appendicitis; perforated appendicitis; blunt abdominal trauma; penetrating abdominal trauma; ruptured abdominal aorta, second operation to drain abscess; etc. The invention also is useful with non-intraabdominal surgeries such as orthopedic surgeries, pelvic and gynecologic surgeries, urologic surgeries, cardiothoracic surgeries, neurosurgeries, plastic and reconstructive surgeries, vascular surgeries, head and neck surgeries, and surgeries to correct wound infections. These listed surgeries are provided only by way of example and are not intended to be limiting.

A subject about to undergo surgery can be a subject scheduled to undergo an elective or non-emergency surgical procedure. Alternatively, a subject about to undergo surgery can be a subject about to have surgery on an emergency basis. Typically, a subject about to undergo surgery includes a subject that is to have a surgical procedure within the next 24 to 48 hours. A subject about to undergo surgery can include a subject that is to have a surgical procedure within the next 2 to 14 days.

A subject that has recently undergone surgery typically includes a subject that already had a surgical procedure in the previous 24 to 48 hours.

The antigens may be administered alone (e.g., in saline or buffer) or using any delivery vehicle known in the art. For instance, the following delivery vehicles have been described: cochleates (Gould-Fogerite et al., 1994, 1996); emulsomes (Vancott et al., 1998, Lowell et al., 1997); ISCOMs (Mowat et al., 1993, Carlsson et al., 1991, Hu et., 1998, Morein et al., 1999); liposomes (Childers et al., 1999, Michalek et al., 1989, 1992, de Haan 1995a, 1995b); live bacterial vectors (e.g., *Salmonella, Escherichia coli, Bacillus Calmette-Guerin, Shigella, Lactobacillus*) (Hone et al., 1996, Pouwels et al., 1998, Chatfield et al., 1993, Stover et al., 1991, Nugent et al., 1998); live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); microspheres (Gupta et al., 1998, Jones et al., 1996, Maloy et al., 1994, Moore et al., 1995, O'Hagan et al., 1994, Eldridge et al., 1989); nucleic acid vaccines (Fynan et al., 1993, Kuklin et al., 1997, Sasaki et al., 1998, Okada et al., 1997, Ishii et al., 1997); polymers (e.g., carboxymethylcellulose, chitosan) (Hamajima et al., 1998, Jabbal-Gill et al., 1998); polymer rings (Wyatt et al., 1998); Proteosomes (Vancott et al., 1998, Lowell et al., 1988, 1996, 1997); sodium fluoride (Hashi et al., 1998); transgenic plants (Tacket et al., 1998, Mason et al., 1998, Haq et al., 1995); virosomes (Gluck et al., 1992, Mengiardi et al., 1995, Cryz et al., 1998); virus-like particles (Jiang et al., 1999, Leibl et al., 1998). Those skilled in the art will recognize that other delivery vehicles that are known in the art may also be used.

Combined with the teachings provided herein, by choosing among the various antigens and their intended use, and weighing factors such as potency, relative bioavailability, patient body weight, severity of adverse side-effects and preferred mode of administration, an effective therapeutic treatment regimen can be planned which does not cause substantial toxicity and yet is entirely effective to treat the particular subject as described above. The effective amount for any particular application can vary depending on such factors as the disease or condition being treated, the particular agent being administered, whether a secondary antigen is also administered and the nature of such antigen (e.g., when the agents are used as adjuvants), the size of the subject, or the severity of the disease or condition. One of ordinary skill in the art can empirically determine the effective amount of a particular formula I or formula II agent and/or other therapeutic agent without necessitating undue experimentation.

For adult human subjects, doses of the formula I and formula II agents typically range from about 50 μg/dose to 20 mg/dose, more typically from about 80 μg/dose to 8 mg/dose, and most typically from about 800 μg/dose to 4 mg/dose. Stated in terms of subject body weight, typical dosages range from about 0.5 to 500 μg/kg/dose, more typically from about 1 to 100 μg/kg/dose, and most typically from about 10 to 50 μg/kg/dose. Doses will depend on factors including the route of administration, e.g., oral administration may require a substantially larger dose than subcutaneous administration.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. Compositions that comprise a pharmaceutically acceptable carrier are generally referred to herein as pharmaceutical compositions.

The formula I and/or formula II agents can be together with other therapeutic agents known in the art to be useful in treating particular conditions. When administered together with another therapeutic agent, formula I/formula II agents can be administered before, with or after administration of the other therapeutic agent.

For example, formula I and/or formula II agents can be administered in combination with anti-bacterial agents, anti-viral agents, anti-fungal agents, and anti-parasitic agents.

Anti-bacterial antibiotic drugs are well known and include, for example: amdinocillin, amikacin, aminoglycosides, amoxicillin, ampicillin, avlocillin, azithromycin, bacampicillin, carbenicillin, cefaclor, cefadoxil, cefamandole, cefazolin, cefmenoxine, cefonicid, cefoperazone, cefotaxime, cefotetan, cefoxitin, ceftazidme, ceftizoxime, ceftriaxone, cefuroxime axetil, cephalexin, cephradine, chloramphenicol, clavulanate, clindamycin, cloxacillin, cyclacillin, dicloxacillin, epicillin, erythromycin, flucloxacillin, gentamicin, hetacillin, imipenem, lincomycin, methicillin, metronidazole, mezlocillin, moxalactam, nafcillin, neomycin, oxacillin, penicillin G, penicillin V, piperacillin, pivampicillin, quinolones, rifampin, sulbactam, tetracyclines, ticarcillin, timentin, tobramycin, trimethoprim-sulfamethoxazole, and vancomycin. (See Goodman and Gilman's *The Pharmacological Basis of Therapeutics,* 9th Ed., 1996, McGraw Hill, Inc.)

Anti-virals include, for instance, but are not limited to acemannan; acyclovir; acyclovir sodium; adefovir; alovudine; alvircept sudotox; amantadine hydrochloride; aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscarnet sodium; fosfonet sodium; ganciclovir; ganciclovir sodium; idoxuridine; interferon alpha (IFN-α); kethoxal; lamivudine; lobucavir; memotine hydrochloride; methisazone; nevirapine; penciclovir; pirodavir; ribavirin; rimantadine hydrochloride; saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zidovudine; and zinviroxime.

Anti-fungals include, for instance, but are not limited to acrisorcin; ambruticin; amphotericin B; azaconazole; azaserine; basifungin; bifonazole; biphenamine hydrochloride; bispyrithione magsulfex; butoconazole nitrate; calcium undecylenate; candicidin; carbol-fuchsin; chlordantoin; ciclopirox; ciclopirox olamine; cilofungin; cisconazole; clotrimazole; cuprimyxin; denofungin; dipyrithione; doconazole; econazole; econazole nitrate; enilconazole; ethonam nitrate; fenticonazole nitrate; filipin; fluconazole; flucytosine; fungimycin; griseofulvin; hamycin; isoconazole; itraconazole; kalafungin; ketoconazole; lomofungin; lydimycin; mepartricin; miconazole; miconazole nitrate; monensin; monensin sodium; naftifine hydrochloride; neomycin undecylenate; nifuratel; nifurmerone; nitralamine hydrochloride; nystatin; octanoic acid; orconazole nitrate; oxiconazole nitrate; oxifungin hydrochloride; parconazole hydrochloride; partricin; potassium iodide; proclonol; pyrithione zinc; pyrrolnitrin; rutamycin; sanguinarium chloride; saperconazole; scopafungin; selenium sulfide; sinefungin; sulconazole nitrate; terbinafine; terconazole; thiram; ticlatone; tioconazole; tolciclate; tolindate; tolnaftate; triacetin; triafungin; undecylenic acid; viridofulvin; zinc undecylenate; and zinoconazole hydrochloride.

The antigens can be administered with anti-microbial antibodies such as but not limited to cytomegalovirus immune globulin, GAMIMUNE® N (Bayer), hepatitis B immune globulin, rabies immune globulin, and Varicella-Zoster immune globulin.

The antigens can also be administered with GM-CSF and IL-4 or crude mycobacterial wall preparations such as Freund's adjuvants.

Pharmaceutical Compositions

The formula I and/or formula II agents can be administered to a subject by any mode that delivers them to the desired site, e.g., mucosal, systemic. "Administering" the pharmaceutical composition of the present invention may be accomplished by any means known to the skilled artisan. Preferred routes of administration include but are not limited to oral, parenteral, intralesional, topical, transdermal, intramuscular, intranasal, intratracheal, inhalational, ocular, vaginal, and rectal.

For oral administration, the agents can be formulated readily by combining with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer *Science* 249:1527 (1990), which is incorporated herein by reference.

The formula I and/or formula II agents may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2 percent w/v); citric acid and a salt (1-3 percent w/v); boric acid and a salt (0.5-2.5 percent w/v); and phosphoric acid and a salt (0.8-2 percent w/v). Suitable preservatives include benzalkonium chloride (0.003-0.03 percent w/v); chlorobutanol (0.3-0.9 percent w/v); parabens (0.01-0.25 percent w/v) and thimerosal (0.004-0.02 percent w/v).

The pharmaceutical compositions of the invention contain a pharmaceutically-acceptable carrier. The term "pharmaceutically-acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

A variety of administration routes are available. The particular mode selected will depend, of course, upon the particular adjuvants or antigen selected (depending upon the method employed), the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer-based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b)

diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Screening Methods

The identification and purification of a CD1d presented antigen facilitates the identification of further antigens that bind to CD1d. One method provided by the invention is a screening method for other CD1d presented antigens based on the ability of a compound to compete with, for example, PPBF for binding to CD1d. Alternatively, variants of formula I or formula II agents can be synthesized and tested for their ability to compete with binding of, for example, PPBF. Compounds so identified may be either agonists or antagonists, depending upon their effect on T cell stimulation following CD1d binding. If the compound is able to compete with PPBF for binding to CD1d and then also activate CD1d restricted T cells, then the compound would be an agonist. If on the other hand it is able to compete with PPBF but not activate CD1d restricted T cells, then it would be an antagonist.

Accordingly, the present invention further provides inhibitors of CD1d-restricted antigen presentation to T-cells, i.e., CD1d blocking agents. A "CD1 blocking agent" is a composition or compound which is capable of blocking the interaction of a CD1-presented antigen with CD1, or of blocking the interaction between CD1:antigen complexes and their cognate T-cell receptors. Blocking agents include (1) agents which bind to CD1, (2) agents which bind to a CD1-presented antigen, (3) agents which bind to a CD1:antigen complex, (4) agents which bind to a T-cell receptor that recognizes a CD1:antigen complex and (5) agents which prevent the processing of a CD1-presented antigen. In preferred embodiments, the CD1 blocking agents of the invention are CD1 d blocking agents and even more preferably, they function by competing with CD1d binding to the CD1d presented antigens of the invention. That is, the agonists and antagonists identified according to the invention are preferably identified by their ability to either substitute for or inhibit the effects of the CD1d presented antigens of the invention.

CD1d antigen presentation can be inhibited by using a CD1d blocking agent to block the ability of a CD1d-restricted antigen to bind to CD1d. As used herein, a CD1d blocking agent is said to "inhibit CD1d-restricted antigen presentation" when the CD1d blocking agent decreases (1) the binding of a CD1d-presented antigen to a CD1d molecule or (2) the binding of a CD1d:CD1d-presented antigen complex to its cognate T-cell receptors. Some CD1d blocking agents are able to block such binding to undetectable levels while other CD1d blocking agents only slightly decrease such binding. CD1d blocking agents include (1) agents which bind to CD1d, (2) agents which bind to the CD1d-presented antigen, (3) agents which bind to the CD1d:antigen complex, and (4) agents which bind to the T-cell receptors that recognize the CD1d:antigen complex. Respective examples of blocking agents include, but are not limited to, (1) polyclonal or monoclonal antibodies which bind to and block the portion of a CD1d molecule that binds a CD1d-presented antigen, (2) polyclonal or monoclonal antibodies which bind to and block the portion of a CD1d-presented antigen that binds CD1d, (3) synthetic oligopeptides that are derived from the CD1d:antigen-binding portion of a T-cell receptor and which bind to and block the portion of the CD1d:antigen complex bound by intact T-cell receptors, and (4) synthetic compounds comprising a CD1d-presented antigen chemically linked to a purified CD1d molecule or a synthetic derivative thereof.

In an alternative method for inhibiting antigen presentation of CD1d-restricted antigens, a CD1d blocking agent can be employed which blocks the interaction of the antigen:CD1d complex with the TCR molecules on the T-cell. By inhibiting the presentation step, the activation of specific subsets of T-cells can be inhibited. DNA molecules encoding TCR polypeptides displayed by T-cells that recognize the CD1d-presented antigens of the invention are isolated according to methods known in the art. Oskenberg, I. R., et al., *Proc. Natl. Acad. Sci. USA* 86:988-992, 1989; Oksenberg, J. R., et al., *Nature* 345:344-346, 1990 and erratum, *Nature* 353:94, 1991; Uematsu, Y., et al., *Proc. Natl. Acad. Sci. USA* 88:534-538, 1991; Panzara, M. A., et al., *Biotechniques* 12:728-735, 1992; Uematsu, Y., *Immunogenet.* 34: 174-178, 1991. The DNA sequence is converted into a polypeptide sequence, and the portion of the polypeptide sequence that corresponds to the antigen-binding variable region of a TCR polypeptide is used to design synthetic oligopeptides that bind CD1d:antigen complexes on APCs, thereby inhibiting antigen presentation. Oligopeptides are chemically synthesized according to standard methods (Stewart and Young, Solid Phase Peptide Synthesis, Pierce Chemical Co., Rockland, Ill., 1985) and purified from reaction mixtures by reversed phase high pressure liquid chromatography (HPLC). Additionally or alternatively, methods for generating anti-TCR antibodies and anti-TCR binding peptides are well known in the art with regard to MHC presentation and can readily be adapted to the herein disclosed CD1d presentation system. Strominger, J. L., *Cell* 57:895-898, 1989; Davis, M. M., and Bjorkman, P. J., *Nature* 334:395-404, 1989.

A skilled artisan can readily employ known methods of antibody generation, as well as rational blocking agent design in order to obtain the blocking agents of the present invention. Harlow, E., and Lane, D., Antibodies: A Laboratory Manual, Cold Spring Harbor Press, Cold Spring Harbor, 1988; Synthetic Peptides: Answers Guide, Freeman, W. H., New York, 1991; Kasprzak, A. A., *Biochemistry* 28:9230-9238, 1989. Additionally or alternatively, libraries of molecularly diverse molecules can be screened for individual member molecules which are CD1d blocking agents. Effective CD1d blocking agents are identified by their ability to inhibit CD1d-mediated T-cell proliferative and/or cytolytic responses using the materials and methods described herein.

EXAMPLES

Here we describe CD1d mediated T cell activation by a sulfated polycyclic hydrocarbon, phenyl-2,2,4,6,7-pentamethyldihydrobenzofuran-5-sulfonyl (PPBF) and several structurally related compounds. This represents a previously unknown class of CD1d-presented antigens. Because this molecule differs substantially in structure from all previously known CD1 presented antigens, this extends the range of known targets of CD1-mediated T cell responses beyond that of conventional glycolipids to include polycyclic hydrocarbons.

Example 1

Isolation of Human CD1d-Restricted T Cells

To generate CD1-restricted T cells that recognize novel antigens, we stimulated human peripheral blood lymphocytes using a method that reduces the outgrowth of MHC-restricted T cells and favors the detection of CD1-restricted T cells. This involves the repeated stimulation of lymphocytes with lipid antigens with monocyte-derived dendritic cells (DC) from donors that differ in their MHC protein expression, so that T cells responding to DC with a given MHC class I or II molecule will not be repeatedly stimulated and therefore be detected in T cell lines produced after many rounds of stimulation. DCs were prepared from the peripheral blood of healthy donors by centrifugation over Ficoll-Hypaque, adherence of the mononuclear cells to plastic tissue culture flasks, culture of adherent cells with 300 U/ml GM-CSF and 200 U/ml IL-4 for 3 days, followed by irradiation (3300 R).

Figure 2:
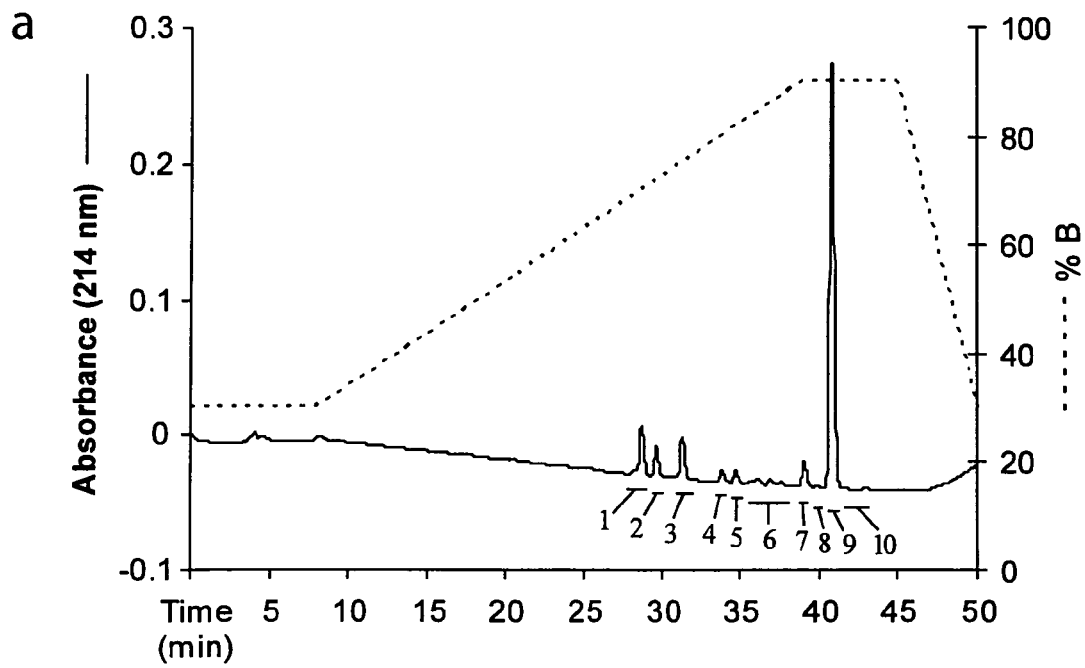
FIG. 2A-B. Fractionation of the LKKRRL mixture.
Figure 2:
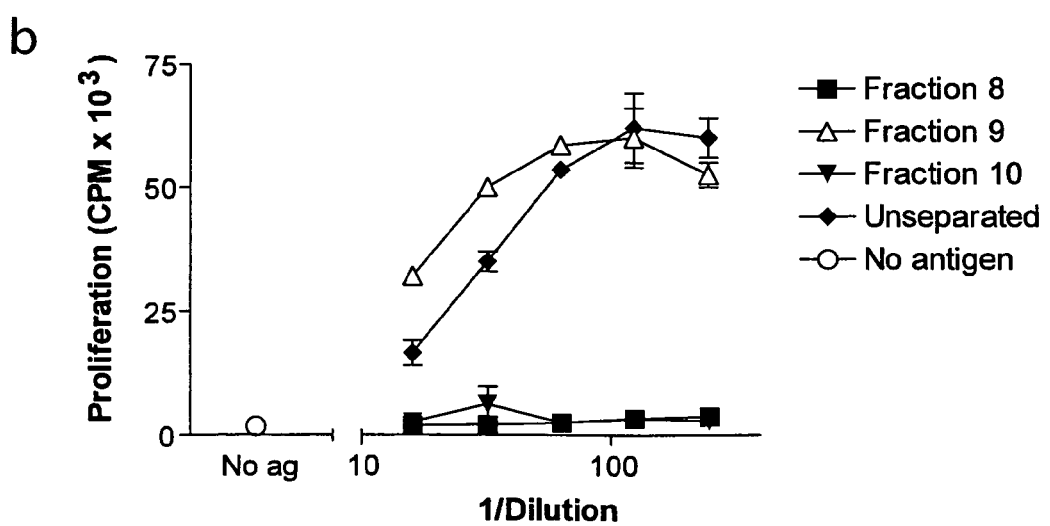

Based on our discovery that lipopeptides can activate T cells, we designed an acyl peptide, LKKRRL (SEQ ID NO:3), which had a modification of a mixture of fatty acids (C14:0, C16:0, C18:0, C18:1, C20:0) on the EC of the third amino acid, a lysine. The lipopeptide was synthesized using standard solid phase techniques by the Anaspec corporation. This antigen preparation was labeled LKKRRL, but initial analysis by liquid chromatography-mass spectrometry (LC-MS) detected at least 10 distinct compounds within this mixture (FIG. 2A). This included a compound corresponding to the mass of LKKRRL, phenyl-2,2,4,6,7-pentamethyldihydrobenzofuran-5-sulfonyl (PPBF), and several compounds whose structures have not been identified. This sample is referred to as the "LKKRRL mixture."

DC and T cells were cultured at a 1:5 ratio in the presence of 1 µg/ml LKKRRL mixture to yield T cell lines. T cells lines were used to generate clones by culturing T cells at approximately 1 cell per well with phytohemagglutinin, peripheral blood mononuclear cells, transformed B cell lines and 2 nM IL-2. This protocol yielded a polyclonal T cell line IL1AP and several clones derived there from, which are named IL1AP.15, IL1AP.31.

Example 2

Proliferative Responses of CD1d-Reactive T Cells

To assay the proliferative responses of IL1AP T cells, $5*10^4$ Polyclonal IL1AP T cells were stimulated with $3*10^4$ DC and LKKRRL mixture (FIG. 1A). IL1AP cells were activated by DCs in a dose dependent manner when the LKKRRL mixture was added. αCD1d antibody, but not antibodies against other CD1 isoforms or isotype control antibody, at a concentration of 20 µg/ml, markedly reduced the stimulation of polyclonal T cells stimulated with 0.5 µg/ml LKKRRL mixture presented by DC (FIG. 1B). This demonstrated that this T cell activation was dependent on the expression of CD1d. C1R cells transfected with the vector pSRα-NEO, containing the cDNAs encoding human CD1a, CD1b, CD1c, CD1d, or no insert (C1R mock) were used as alternative APC for the stimulation of polyclonal T cells with LKKRRL mixture (FIG. 1C). The results of this experiment further confirm the CD1d-dependent nature of the T cell response. Anti CD1a monoclonal antibody clone OKT6, CD1b BCD1b.3, CD1c F10/21A3.1, CD1d CD1d42, and P3, an antibody of unknown specificity as an isotype control, were used for these studies.

Subsequent studies found that several clones derived from IL1AP were also stimulated by the compounds present in LKKRRL and that their responses could be inhibited by monoclonal antibodies that bind human CD1d proteins (data not shown).

Example 3

Isolation of Antigenic Compounds

Initial chromatographic characterization of the LKKRRL mixture demonstrated that at least 10 separable compounds were present in the mixture. To determine the precise chemical identity of the compound or compounds which stimulated the CD1d-mediated T cell response, the mixture was subjected to separation by reverse phase high performance liquid chromatography (FIG. 2A). After loading onto a C18 column with an internal diameter of 4.6 mm (Vydac), compounds were resolved by a gradient of decreasing amounts of solvent A (20% acetonitrile, 80% water, 0.02% TFA) in solvent B (50% methanol, 30% acetonitrile, 20% water), with a flow rate of 0.7 ml/minute. Ten individual fractions were collected and tested for their ability to stimulate IL1AP T cells. Among the 10 fractions tested, only fraction number 9 activated T cells (FIG. 2B).

Example 4

Structural Determination of Antigenic Compounds

Figure 3:
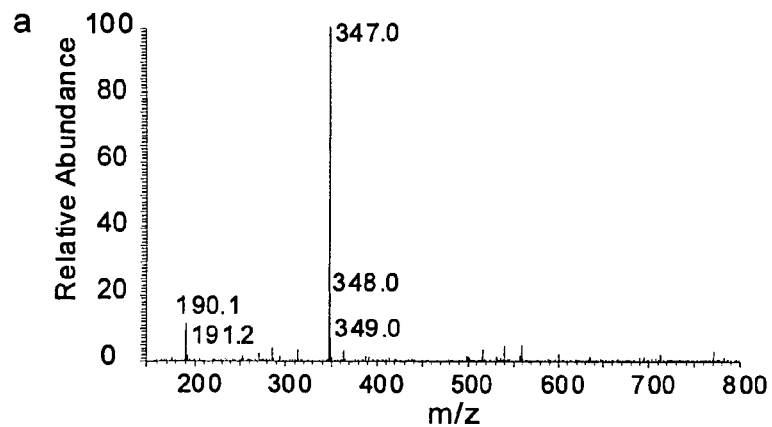
FIG. 3A-C. Structure of the CD1d antigen.
Figure 3:
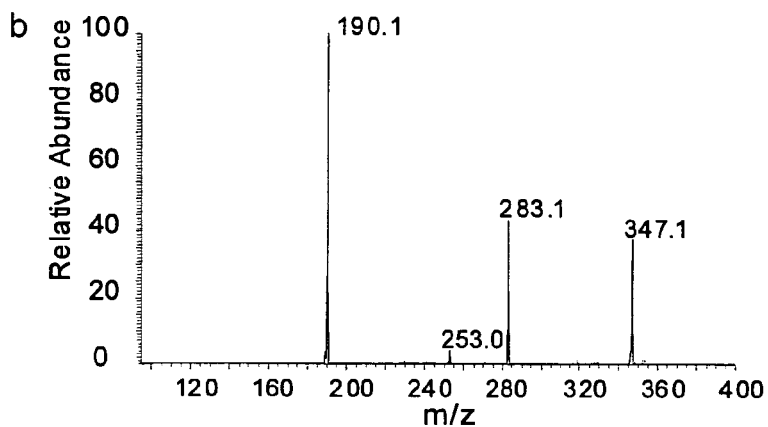
Figure 3:
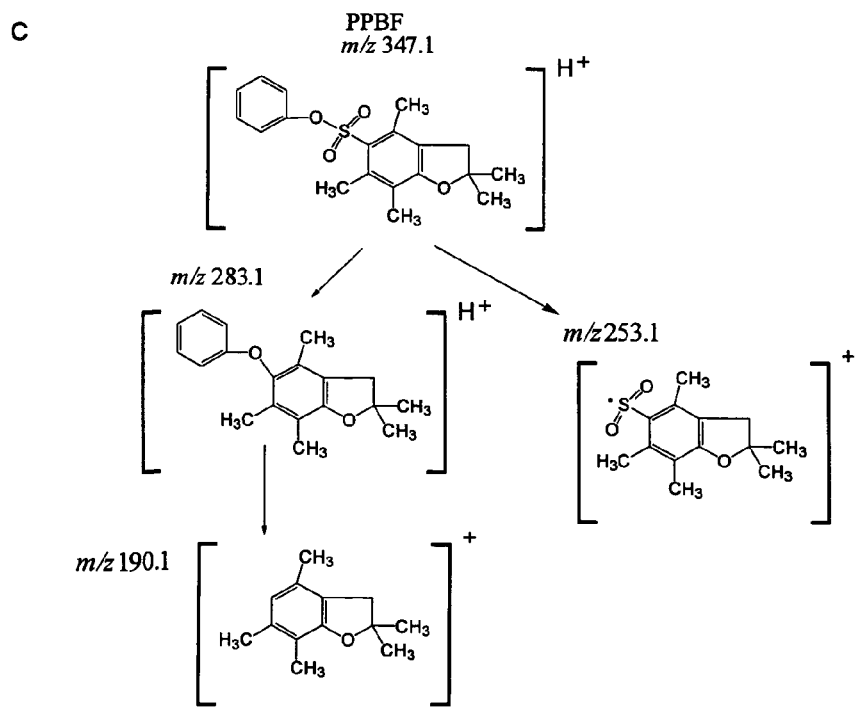

Mass spectral (MS) analysis of the compounds in fraction 9 identified several ions in the positive mode. Prominent among these was a singly charged positive ion of m/z 347.0, which corresponds to a molecular weight of 347, which is hereafter referred to as antigen 347 (FIG. 3A). Tandem mass spectral analysis (MS/MS) of the ion at m/z 347 showed that it gave rise to prominent product ions of m/z 190.1, 252.9 and 283.1 (FIG. 3B). Detection of a relatively strong MS signal at m/z 349, which corresponds to the M+2 ion of antigen 347, showed that the intact molecule contained an atom that naturally occurs with abundant M+2 isotopes, which is commonly seen with sulfur. Thus, antigen 347 likely contained a single sulfur atom. These data, and the fact that the LKKRRL mixture was prepared using phenol and a sulfur-containing derivative of arginine, $N^α$-(9-Fluorenylmethyloxycarbonyl)-$N^γ$-2,2,4,6,7-pentamethyldihydrobenzofuran-5-sulfonyl-L-arginine (Fmoc-L-Arg(PBF)-OH), indicated that antigen 347 could correspond to a phenolic derivative of PBF. This compound, which we refer to as phenyl-2,2,4,6,7-pentamethyldihydrobenzofuran-5-sulfonyl, or PPBF, is shown in FIG. 3C. PPBF has a predicted mass of 346.12, which when occurring as a proton adduct, should yield an ion m/z 347.12. Thus, the predicted mass of PPBF corresponded to the predominant ion detected in fraction 9 of LKKRL with an error that is less that known to occur with the mass spectral technique. That the antigenic compound in fraction 9 of the LKKRRL mixture has a structure similar or identical to that shown in FIG. 3C, was strongly supported by tandem mass spectrometric (MS/MS) analysis of antigen 347, which detected ions of m/z 283, 253, and 190, corresponding to fragments shown in FIG. 3C.

Figure 4:
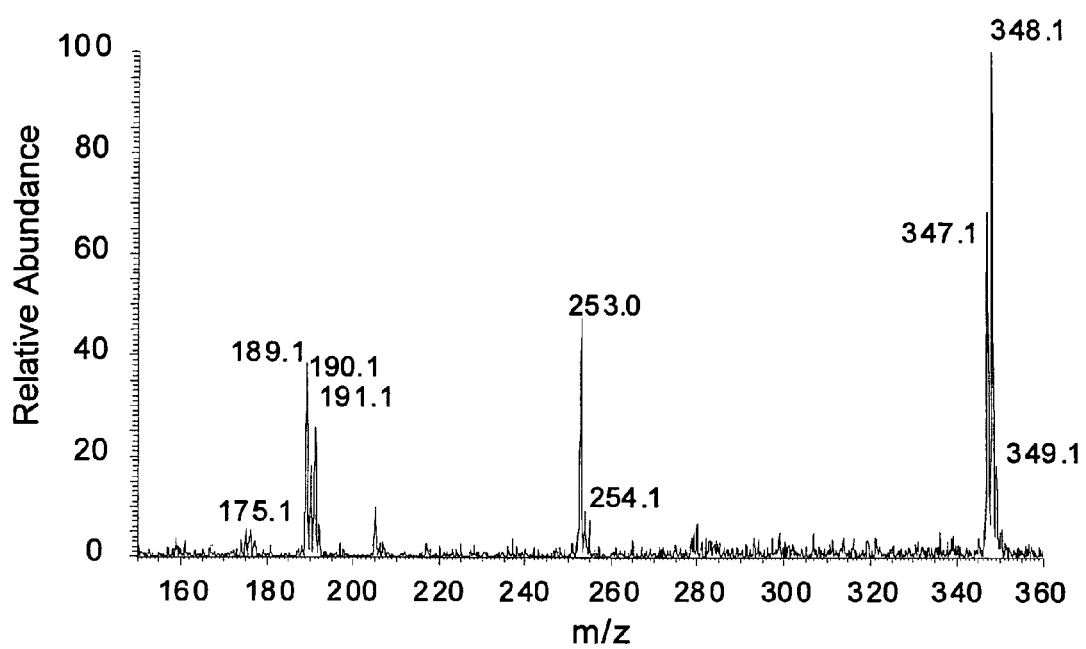
FIG. 4 is a graph depicting mass spectral analysis of deuterated PPBF.

PPBF was incubated overnight in acetonitrile with 1% deuterated water and analyzed by MS. Deuterium exchange showed that antigen 347 did not contain any exchangeable protons, consistent with the lack of free hydroxyl or amide protons (FIG. 4).

Figure 5:
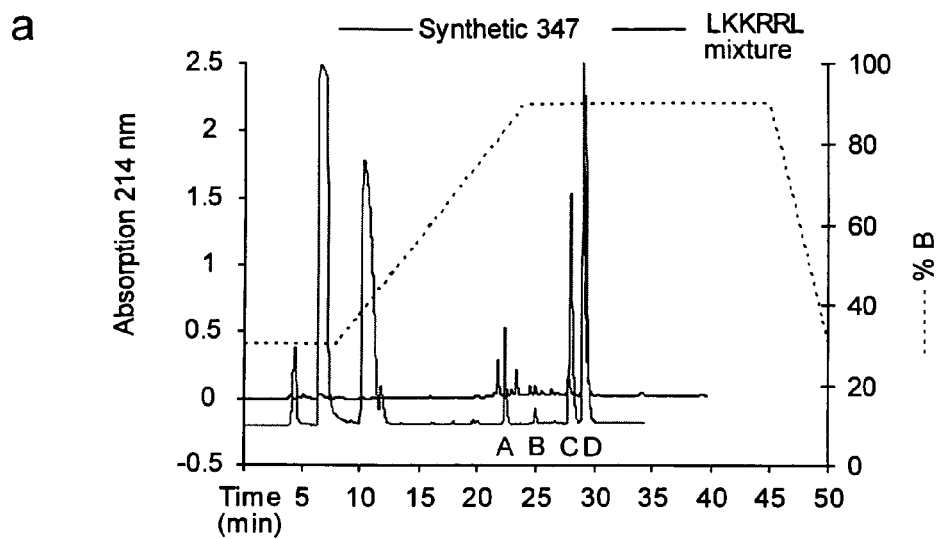
FIG. 5A-C. Fractionation of a synthetic PPBF mixture.
Figure 5:
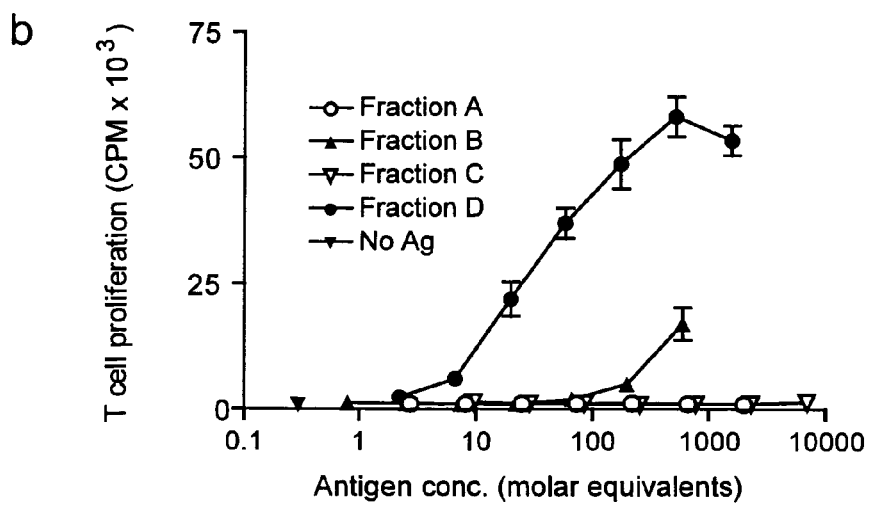
Figure 5:
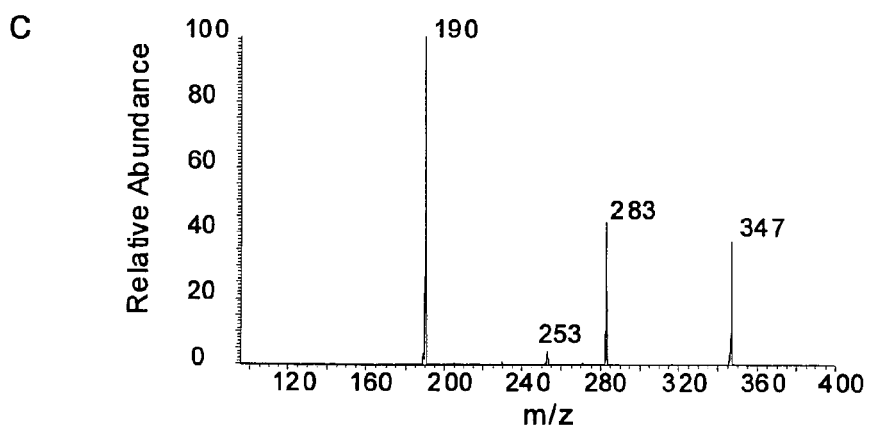

To independently confirm that PPBF from another source could stimulate T cells, PPBF was synthesized from Fmoc-L-Arg(PBF)-OH and phenol to produce "synthetic PPBF." This was done by incubating a mixture of 10 mg phenol, 10, mg Fmoc-L-Arg(PBF)-OH, 100 µl trifluoracetic acid (TFA), and 100 µl chloroform overnight at room temperature. HPLC analysis of the reaction mixture showed that it contained a compound that precisely co-eluted with fraction 9 from the LKKRRL mixture (FIG. 5A, peak D). Further analysis of peak D showed that it ionized in the positive mode with a prominent ion at m/z 347, which corresponded to the predicted molecular weight of PPBF. Direct comparison of the chemical properties of lipids derived from LKKRRL and synthetic PPBF showed that both molecules had identical retention times by HPLC, the same mass and similar collisional mass spectral profiles. Therefore, PPBF from LKKRRL and synthetic PPBF had the same chemical structure.

Synthetic PPBF was found to potently stimulate a CD1d-mediated response of IL1AP (FIG. 6E, open circles and FIG. 7A, triangles), proving the chemical identity of the CD1d-mediated antigen from an independent source of PPBF. Because fraction 9 of LKKRRL and synthetic 347 have the same chemical and immunological properties, they are both subsequently referred to by their chemical name, PPBF.

Example 5

Figure 6:
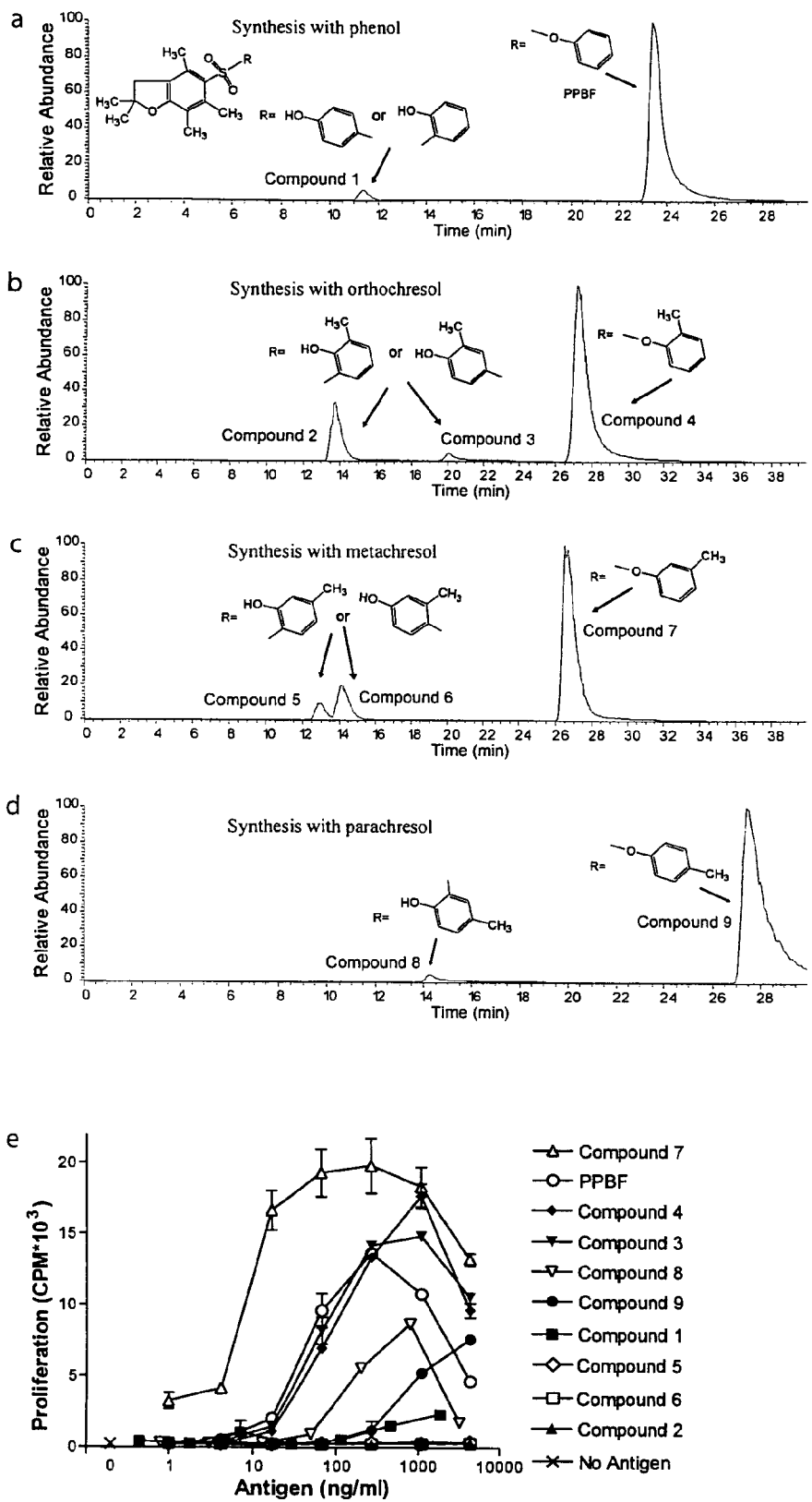
FIG. 6A-E. Structure and activity of synthetic PPBF analogs.

Synthesis of PPBF Analogs and the Influence of Chemical Structure on T Cell Activation Nine PPBF analogs were synthesized by using Fmoc-L-Arg(PBF)-OH and chresol (methyl phenol) instead of phenol in the synthesis mixture. Different series of PPBF-related compounds were synthesized using chresol with the methyl group in the ortho, meta or para configuration. The O—S linkage is predicted to be most efficiently formed, but and C—S linkage involving aromatic carbons in the ortho and para position relative to the hydroxy-group also occurs. The synthesis mixtures were separated by reverse phase HPLC/MS, and fractions containing the predicted ions were collected. The structures of the PPBF analogs and tandem mass spectral analysis is shown in FIGS. 6A-6D. The relative capacity of these analogs to stimulate IL1AP T cell proliferation are shown in FIG. 6E. The data show that several of the compounds stimulated IL1AP T cells as potently, or more potently than PPBF, while several compounds did not stimulate as potently as PPBF. For example, 3-methyl-PPBF (compound 7) stimulated T cells more potently than PPBF (FIG. 6E, compare open triangles and open circles).

Example 6

Stimulatory Properties of PPBF are Specific and Distinct from Those of αGalCer

Conventionally, CD1d-restricted T cells are classified as invariant NK T cells or varied CD1d-restricted T cells. Human invariant NK T cells are activated by αGalCer and express TCRs that have a Vα24 variable region.

Figure 7:
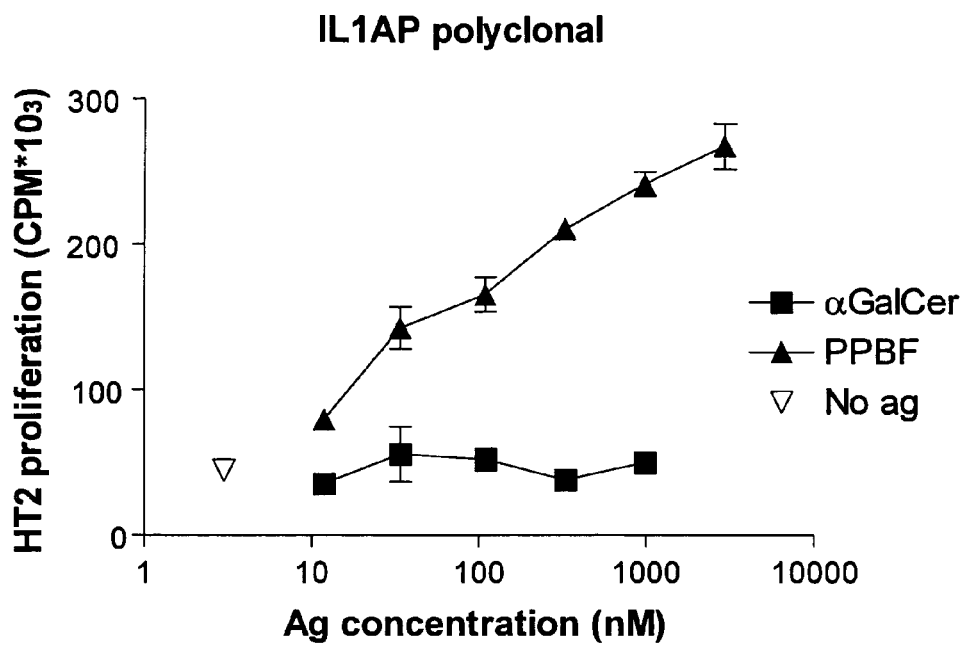
FIG. 7A-B. Specificity of CD1d-reactive T cells.
Figure 7:
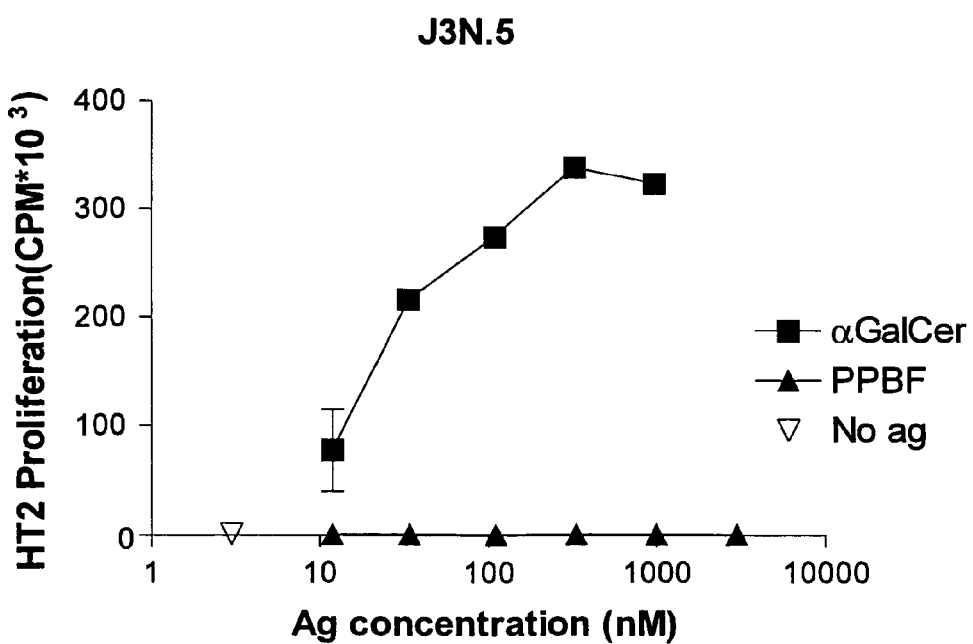

Because αGalCer was previously known to function as a potent activator of CD1d-restricted T cell clones known as NK T cells, we sought to determine whether PPBF-reactive T cells and αGalCer-reactive T cells cross react. The PPBF-reactive T cell line IL1AP and the αGalCer-reactive T cell clone J3N.5 were each stimulated with αGalCer and PPBF using DC as APC. IL-2 release was measured 24 h after stimulation. The IL-2 concentration in 50 µl of culture supernatants, harvested 24 hours after T cell stimulation, was determined by adding $10^4$ IL-2 starved HT-2 cells in 100 ml medium, and a 6 h pulse after a 24 h incubation. PPBF-reactive T cells did not recognize αGalCer (FIG. 7A). The αGalCer-reactive NK T cell clone J3N.5 was not activated by PPBF (FIG. 7B).

To determine whether PPBF non-selectively activated polyclonal lymphocyte populations or selectively activated antigen-specific clones present at low precursor frequency in vivo, polyclonal lymphocytes were tested for their proliferative response to PPBF. In all cases, polyclonal T cells and T cell clones were activated by the mitogen phytohemagglutinin, demonstrating that the clones were capable of being activated, but not by PPBF (data not shown). Only the T cell line IL1AP and clones derived therefrom were activated by PPBF. These data provide evidence that PPBF activated certain human T cells in a CD1d-dependent manner.

Figure 8:
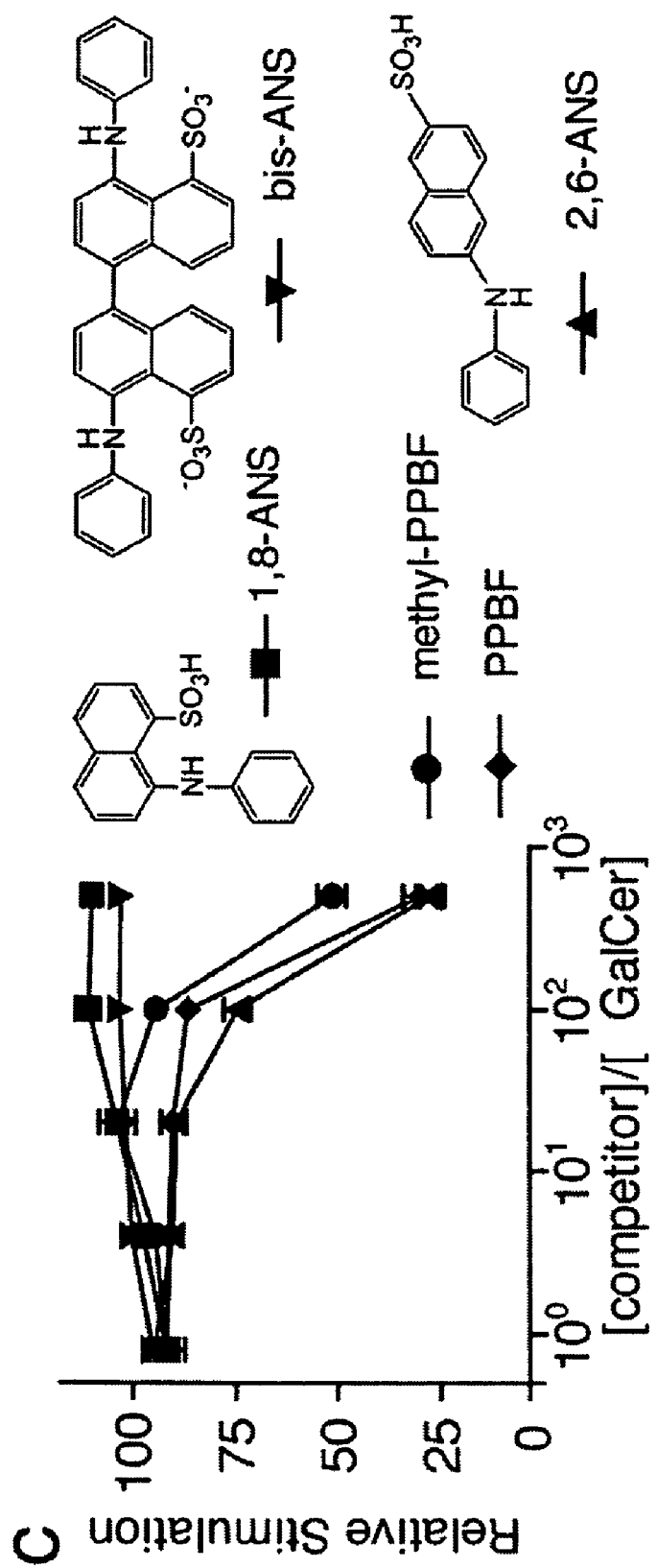
FIG. 8. PPBFs do not stimulate NK T cells.

Next, to determine whether PPBF could compete with αGalCer-mediated NK T cell responses, we used an in vitro assay of PPBF added to recombinant CD1d proteins bound to a plate. When added in excess, PPBF and 3-methyl PPBF were both found to substantially block αGalCer-mediated NK T activation in a dose-dependent manner (FIG. 8). The degree and titer at which the PPBF and 3-methyl PPBF inhibited αGalCer-mediated NK T activation were comparable to that of 2,6-anilonapthalene sulfonic acid (ANS), a polyaromatic hydrocarbon that has been shown to bind CD1d (Im et al., *J Biol Chem.*, 279:299-310, 2004). The structure of 2,6-ANS and other ANS compounds used as controls are shown in FIG. 8. These data provide further evidence that NK T cells have a different antigen specificity than IL1AP T cells, and that PPBFs and αGalCer compete for CD1d-mediated T cell activation.

Example 7

Receptors on PPBF-Reactive T Cells

The polyclonal T cell line IL1AP and different clones derived therefrom were analyzed by flow cytometry. IL1AP cells were stained with anti-TCRαβ-FITC, clone WT31-FITC from Becton Dickinson (FIG. 9A), and anti-CD4-FITC, clone RPA-T4-FITC from Pharmingen (FIG. 9B), and FITC-labeled isotype control antibody (thin lines).

Figure 9:
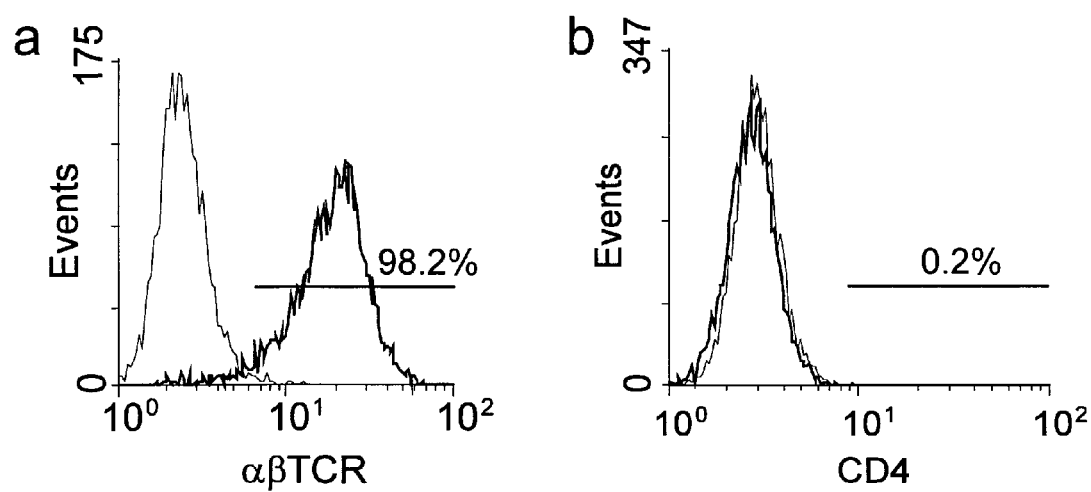
FIG. 9A-B. Phenotypic analysis of IL1AP T cells.

All PPBF-reactive T cells were found to stain with the OKT3 antibody that recognizes a conformation-dependent epitope on CD3-6 and with anti-TCRαβ-FITC (FIG. 9A), but not with an antibody against CD4 (FIG. 9B).

To directly examine whether the responses observed with PPBF were T cell receptor (TCR) mediated, we determined the sequences of the T cell antigen receptor α and β chains and expressed them to see if transfection conferred responsiveness to PPBF. Complementary DNA for the α and β chains was isolated from several clones as follows. mRNA was isolated from 1*10E6 cells of polyclonal IL1AP T cells and T cell clones IL1AP.17 and 28, using an Oligotex Direct mRNA kit (Qiagen), followed by cDNA synthesis using SuperScript RT (Invitrogen). A PCR-primer set covering the TCR Vα/Vβ families was used to determine the Vα/Vβ usage (FIG. 10A). The polyclonal T cell line IL1AP and two clones, IL1AP.17 and IL1AP.28, gave a single PCR band when primed with Vα2 or Vβ21 primer sets (FIG. 10A). For the positive Vα/Vβ pair, primers that cover the full length α and β chains were used to obtain a PCR product that was cloned into the pCR-4-TOPO vector (Invitrogen). These products were sequenced and all α and all β chain sequences were identical, and corresponded to Vα2, or TRAV12-1*01 (imtg nomenclature), joined with TRAJ6*01 (FIG. 10B), and Vβ21 or TRBV11-3*01 (imtg nomenclature), joined with TRBJ2-5 (FIG. 9C). Sequencing was performed with M13-reverse and T7 primers. The sequences shown in FIG. 10B and FIG. 10C were derived twice from the polyclonal T cell line and twice from the clones that were used. The α chain is shown in FIG. 10B: base 1-337: TRAV12-1*01; base 338-342: N nucleotides; base 343-400: TRAJ6*01; base 401: beginning of CA. The β chain is shown in FIG. 10C: base 1-402: TRBV11-3*01; base 403-411: N nucleotides and TRBD01*01; base 412-456: TRBJ2-5; base 457: beginning of CB.

This TCR α and β chain pair is distinct from sequences that are found in human CD1d-restricted NK T cells, providing further evidence that this is a T cell stimulating activity that is distinct from that involving αGalCer and NK T cells.

We transfected the full-length TCR α and β chains from IL1AP cells into J.RT3 cells to generate a TCR-expressing reporter cell line (J.RT3.ABd). Transfection of both TCR α and β chains from IL1AP cells reconstituted surface CD3 complexes and conferred the ability to produce IL-2 upon stimulation with PPBF (FIG. 11A). To determine whether PPBF could activate through intact CD3 complexes that were reconstituted by transfection of a TCR with irrelevant antigen specificity, J.RT3-T3.5 cells transfected with the TCR α and β chains of the CD8-2 cell line (J.RT3-CD8-2) that recognizes the mycobacterial lipopeptides DDM were tested for IL-2 release upon stimulation with DDM or PPBF. As shown in FIG. 11B, the cells released IL-2 in response to DDM but not PPBF.

A number of embodiments of the invention have been described. Nevertheless, it will be understood that various modifications may be made without departing from the spirit and scope of the invention. Accordingly, other embodiments are within the scope of the following claims.

What is claimed is:

1. A method for activating a CD1d-restricted T cell comprising an α:β T cell receptor (TCR), the method comprising:

contacting the CD1d-restricted T cell with an antigen-presenting cell (APC), wherein the APC comprises CD1 molecules, and phenyl-2,2,4,6,7-pentamethyldihydrobenzofuran-5-sulfonyl (PPBF) in vitro, thereby activating the T cell.

2. The method of claim 1, wherein the T cell is from a subject.

* * * * *